(12) United States Patent
Maksimov et al.

(10) Patent No.: US 6,690,705 B2
(45) Date of Patent: Feb. 10, 2004

(54) METHOD AND APPARATUS FOR EXCITATION OF CHEMICAL BONDS

(75) Inventors: Aleksander Maksimov, La Spezia (IT); Peter Novak, Antwerp (BE)

(73) Assignee: Vector Enery Corporation, Ft. Lauderdale, FL (US)

( * ) Notice: Subject to any disclaimer, the term of this patent is extended or adjusted under 35 U.S.C. 154(b) by 72 days.

(21) Appl. No.: 10/040,598

(22) Filed: Nov. 9, 2001

(65) Prior Publication Data

US 2003/0099271 A1 May 29, 2003

(51) Int. Cl.$^7$ ................................................ H01S 3/09
(52) U.S. Cl. ....................................................... 372/69
(58) Field of Search ...................... 372/19, 69; 436/173

(56) References Cited

U.S. PATENT DOCUMENTS 5,016,064 A   5/1991  Goronkin 6,451,616 B1 * 9/2002 Odom et al. ................ 436/173

* cited by examiner

*Primary Examiner*—Leon Scott, Jr.
(74) *Attorney, Agent, or Firm*—Akerman Senterfitt

(57) ABSTRACT

A method for exciting chemical bonds in molecules using an electromagnetic field includes the step of generating a plurality of electromagnetic oscillation modes. The oscillation modes redistributing respective mode energies between themselves. Energy derived from the redistributed mode energies is used to impart energy to at least one pair of electrons comprising a chemical bond, thus exciting these electrons. The process can be used even when all electrons are paired. The method can be used for synthesizing compounds, quantum mechanical pumping of chemical bonds and for characterization of materials. An apparatus for exciting chemical bonds in molecules using an electromagnetic field includes a structure for generating a plurality of electromagnetic oscillation modes, the oscillation modes redistributing respective mode energies between themselves. The structure for generating a plurality of electromagnetic oscillation modes preferably includes a self-sustained oscillation system having distributed parameters.

35 Claims, 12 Drawing Sheets

THE DISTRIBUTION OF CURRENT J IN RECTANGULAR RESONATOR WITH THE MODE TE$_{102}$

THE GRAPHS OF FUNCTIONS $A_1 = \int_{r-at}^{r+at} e^{-\alpha r} \sin[kr] dr$ and $A_2 = \int_{r-at}^{r+at} dr \int_{r-at}^{r+at} e^{-\alpha r} \sin[kr] dr$ THE GRAPH OF FUNCTION $A_1 = \int_{r-at}^{r+at} \frac{\sin[kr]}{\pi r} dr$ THE GRAPH OF FUNCTION $A_2 = \int_{r-at}^{r+at} dr \int_{r-at}^{r+at} \frac{\sin[kr]}{\pi r} dr$ THE GRAPH OF FUNCTION $Re[A_1] = Re\left[\int_{r-at}^{r+at} \frac{ke^{-ikr}}{\pi(k^2 r^2 + 1)} dr\right]$ THE GRAPH OF FUNCTION $Im[A_1] = Im\left[\int_{r-at}^{r+at} \frac{ke^{-ikr}}{\pi(k^2 r^2 + 1)} dr\right]$ THE GRAPH OF FUNCTION $\mathrm{Re}[A_2]= \mathrm{Re}\left[\int_{r-at}^{r+at}dr\int_{r-at}^{r+at}\dfrac{ke^{-ikr}}{\pi(k^2r^2+1)}dr\right]$ THE GRAPH OF FUNCTION $Im[A_2] = Im\left[\int_{r-at}^{r+at} dr \int_{r-at}^{r+at} \frac{ke^{-ikr}}{\pi(k^2r^2+1)} dr\right]$

THE FORMS OF PULSES IN THE CONCURRENCE OF MODES CONDITION

THE DISTRIBUTION OF CURRENT J IN RECTANGULAR RESONATOR WITH THE MODE $TE_{102}$

THE ESR-SPECTRUM FROM $3d^1$-ELECTRON STATES OF VANADIUM IONS IN $Na_{0.22}V_2O_5$, T>200K

THE ESR-SPECTRUM FROM $3d^1$-ELECTRON STATES OF VANADIUM IONS IN $Na_{0.22}V_2O_5$, T=140K

METHOD AND APPARATUS FOR EXCITATION OF CHEMICAL BONDS

BACKGROUND OF THE INVENTION

In general, the possible effects of an externally applied electromagnetic field on an atomic or molecular system may be reduced to the following [3]:

1. Stimulated emission or absorption of the electromagnetic radiation, and
2. Inducement of electric and magnetic moments.

Stimulated emission/absorption of electromagnetic radiation occurs when the electromagnetic wave frequency $\omega$ corresponds to the splitting of atomic or molecular energy levels so that the equation $\hbar\omega = \Delta E$ is satisfied.

A response of an electron or group of electrons to an electromagnetic field generally requires a magnetic moment. Although electrons taken in isolation produce a magnetic field as they spin and orbit the nucleus, two electrons of the external electron shell of the atom with opposite spins producing a net magnetic moment, which can be zero. For example, a He atom has two electrons spinning and orbiting around the nucleus. The two electrons have equal but opposite in sign spins (proper magnetic moments) and therefore the total magnetic moment produced by these electrons is equal to zero.

Similarly, chemical bonds, which result from the sharing of electrons between atoms result in no net magnetic moment for the shared electrons making up the chemical bond. As a result, under normal conditions, electrons, which form chemical bonds, do not respond to electromagnetic fields, such as in response to an electron spin resonance (ESR) experiment, because their effective magnetic moment is equal to zero.

SUMMARY OF THE INVENTION

A method for exciting chemical bonds of molecules using an electromagnetic field, includes the steps of generating a plurality of electromagnetic oscillation modes, the oscillation modes redistributing respective mode energies between themselves, and transferring energy derived from the redistribution of mode energies to at least one pair of electrons comprising a chemical bond.

The oscillation modes can interact to form a resulting electromagnetic field, the resulting electromagnetic field characterized by a vector potential which oscillates in time, does not have spatial oscillations, and has an amplitude which decreases with distance. The transferring step can induce a magnetic moment the chemical bonding electrons. The method can include the step of providing a self-sustained oscillation system with distributed parameters for the generating step. The self-sustained oscillation system can include a generator of SHF radiation loaded on a reflecting cavity resonator, a reentrant cavity resonator or an open (optical) resonator.

A method of synthesizing compounds can include the steps of generating a plurality of electromagnetic oscillation modes, the oscillation modes redistributing respective mode energies between themselves and applying at least a portion of the redistributed mode energy to at least one reagent. The redistributed mode energy can increase the rate of formation of at least one chemical bond involving the first reagent compared to the formation rate in the absence of the redistributed mode energy. At least one reagent includes at least a first and second reagent.

The method can be used to formation crystalline material. The method further include the step of controlling the applying step to produce selected magnetic or dielectric properties of the crystalline material, the properties attained being different from inherent ones of the properties of the material. The crystalline material can be a single crystal material.

A method for electromagnetically pumping chemical bonds includes the steps of generating a plurality of electromagnetic oscillation modes, the oscillation modes redistributing respective mode energies between themselves, applying at least a portion of the redistributed mode energy to at least one object having at least one naturally occurring anisotropic structural, mechanical or electromagnetic parameter, and modifying at least one of the anisotropic parameters upon transfer of at least a portion of the redistributed mode energy to the object. The modifying step can include changing the equilibrium energy level distribution of electrons involved in formation of chemical bonds in the object and result in population inversion.

Population inversion can be used to produce stimulated electromagnetic emission from the object. The anisotropic electromagnetic parameters can be dielectric constant, electrical conductivity or thermo-EMF.

A method for characterizing materials includes the steps of generating a plurality of electromagnetic oscillation modes, the oscillation modes redistributing respective mode energies between themselves, ttransferring energy derived from the oscillation modes to impart energy to at least one pair of electrons including a chemical bond of a material, applying a stimulating probing signal to the material and obtaining a spectrum from the material responsive to the probing signal. The electrons of the material can all be paired and the material can be in-vivo, such as bacteria.

An apparatus for exciting chemical bonds in molecules using an electromagnetic field includes a structure for generating a plurality of electromagnetic oscillation modes, the oscillation modes redistributing respective mode energies between themselves, wherein energy derived from the redistributed mode energy is transferred to at least one pair of electrons including a chemical bond. The modes can interact to form a resulting electromagnetic field, the resulting electromagnetic field characterized by a vector potential which oscillates in time, does not have spatial oscillations, and has an amplitude which decreases with distance. The self-sustained oscillation system can have distributed parameters, such as a generator of SHE radiation loaded on a reflecting cavity resonator, a reentrant cavity resonator and an open (optical) resonator.

BRIEF DESCRIPTION OF THE DRAWINGS

A fuller understand of the present invention and the features and benefits thereof will be accomplished upon review of the following detailed description together with the accompanying drawings, in which.

DETAILED DESCRIPTION

Molecules consist of atoms connected by chemical bonds being generally characterized as being either covalent bonds or ionic bonds. Under normal conditions, electrons, which form chemical bonds, do not respond to electromagnetic fields because their net effective magnetic moment is equal to zero.

The invention deals with excitation of chemical bonds electrons with electromagnetic radiation by generating and applying an appropriate electromagnetic field to electrons involved in chemical bonds formation. Although electromagnetic excitation of unpaired electrons is a well-known phenomenon and is a basis for methodologies such as electron spin resonance (ESR), excitation of chemical bonds is made possible by the invention.

Figure 10:
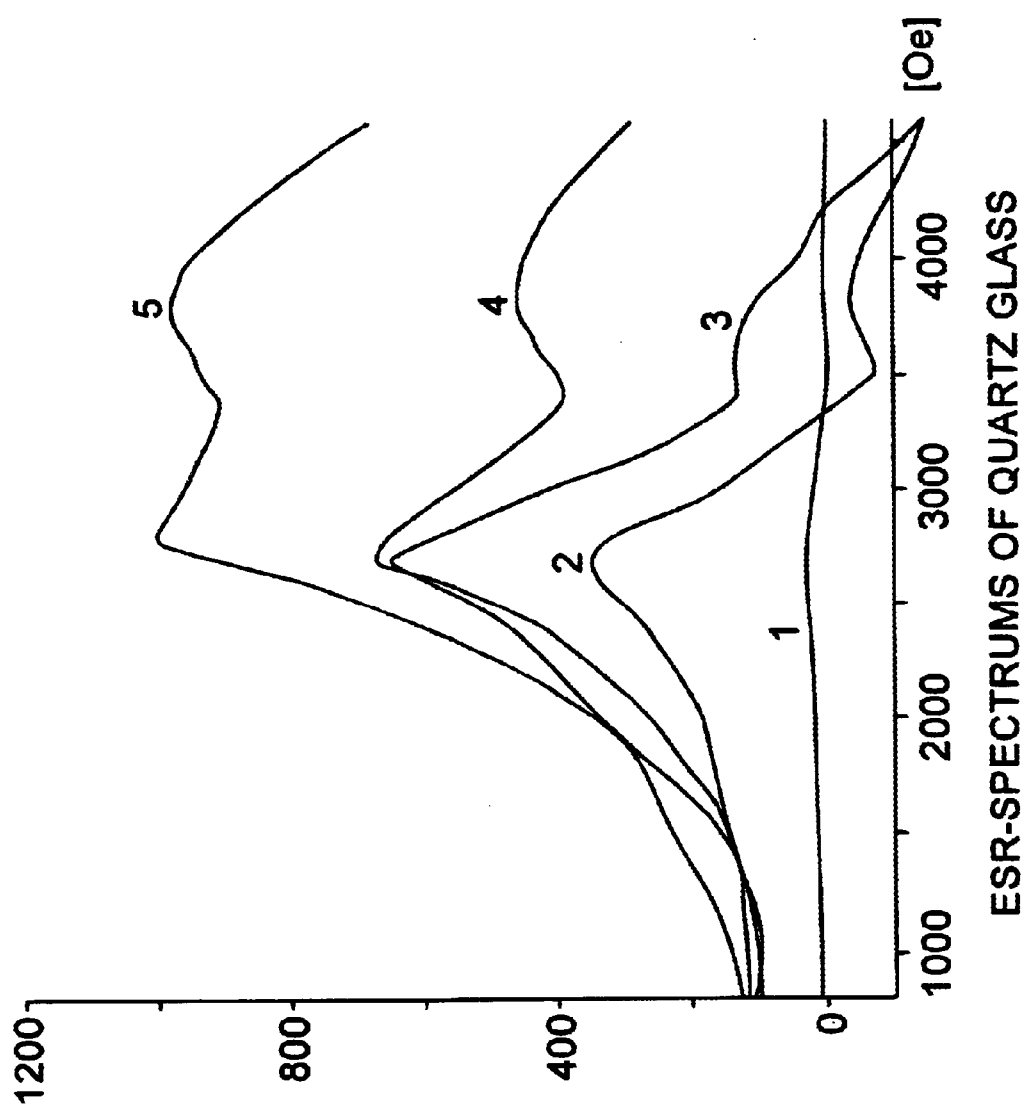
FIG. 10 illustrates ESR spectrums of quartz placed on a rectangular resonator under a variety of conditions.

Although not seeking to being bound by the theoretical explanation presented herein, the invention is believed to operate when an electromagnetic field or wave with the vector potential ($\vec{A}$), which satisfies certain conditions, is applied to chemical bond electrons of molecules. An electromagnetic field or wave with an appropriate vector potential ($\vec{A}$) has been shown to be-capable of chemical bond excitation, as evidenced by eliciting an electron spin resonance response from electrons comprising chemical bonds of $SiO_2$ (FIG. 10).

By defining the parameters of the wave function of chemical bond electrons and determining the parameters of appropriate vector potentials ($\vec{A}$) to excite these electrons, chemical bonds can be excited by externally applied electromagnetic fields. The electromagnetic field with appropriate vector potentials ($\vec{A}$) for exciting of chemical bonds can be generated by a self-sustained oscillation system with distributed parameters operating in a concurrence of mode condition. In this condition, electric and magnetic moments are induced on chemical bond electrons and change the symmetry of resultant wave function of the chemical bond. This effect leads to the electromagnetic excitation of the chemical bonds. Emergence of induced moments does not generally depend on the frequency of electromagnetic field and occurs from extremely low frequencies (such as approaching zero) up to infrared frequencies (or even x-ray frequencies) /3/. This effect can be understood by defining parameters of vector potential $\vec{A}$ for an electromagnetic field and the parameters of the wave function of the chemical bonds. By the controlled variation of the parameters of vector potential $\vec{A}$, which is an integral characteristic of an externally applied electromagnetic field, it is possible to excite chemical bonds.

Although the electromagnetic field is commonly referred to, the electromagnetic field is not the most fundamental field, but is something that is separated from but related to, a more fundamental field. The vector potential, or $\vec{A}$ field, is well known in particle physics but usually ignored in engineering. For example, a magnetic field is created (and defined) by $\vec{\nabla} \times \vec{A} = \vec{B}$. Looking at the vector cross product, by definition, $\vec{B}$ is the line integral about a small surface of the $\vec{A}$ flux through that surface. That is precisely what a single coil of wire, with an electrical current flowing through it, does and therefore creates a magnetic field inside the surface.

In order to describe electromagnetic fields in a free space it is generally accepted to use Hertz potentials /1/. To describe electromagnetic fields in curvilinear coordinates Debyes potentials /2/are generally used. To describe the interaction between electromagnetic fields and matter, vector potential $\vec{A}$ and scalar potential $\phi$ /3/are used.

The action of an external electromagnetic field on particles with mass m and charge e is described /3/by Hamiltonian operator $\hat{H}$:

$$\hat{H} = \hat{H}_0 + \hat{H}'$$

Where $\hat{H}_0$ is an operator of an atomic or molecular system having internal potential energy V in the absence of electromagnetic field:

$$\hat{H}_0 = -\sum_j \frac{\hbar^2}{2m_j} \vec{\nabla}_j^2 + V$$

Operator $\hat{H}'$ describes the action of the electromagnetic field on the system:

$$\hat{H}' = \sum_j \left[\frac{1}{2m_j}\left(i\hbar \frac{e}{c}\vec{\nabla}_j * \vec{A}_j + 2i\hbar \frac{e}{c}\vec{A}_j * \vec{\nabla}_j + \frac{e^2}{c^2}|\vec{A}_j|^2\right) + e_j\varphi_j\right] \quad 5$$

Where $\vec{A}$—vector potential, $\phi$—scalar potential.

The dependence of the wave function of electrons in an atom $\Psi_n(r,t)$ as a function of time can be written as:

$$\Psi_n(r,t) = \psi_n(r)e^{i\frac{E_n}{\hbar}t}$$

The function $\psi_n(r)$ describes dependence of the wave function of electrons in the atom as a function of spatial coordinates and can be expressed as /4,5/:

$$\psi_n(r) = Nr^{(n^*-1)}e^{-\alpha r}Y(\theta, \phi)$$

Where N is a normalizing multiplier, $Y(\theta,\phi)$, the normalizing multiplier being functions of spherical harmonics, $n^*$ is the effective quantum number, and $\alpha$ is the real attenuation constant. The real attenuation constant $\alpha$, is given by:

$$\alpha = \frac{Z-s}{n^* a_0}$$

Where s is the screening constant, Z is the nucleus charge, and $\alpha_0$ is the Bohr radius. In case of hydrogen-like atom $\alpha$:

$$\alpha = \frac{Z}{na_0}$$

Where Z is the nucleus charge and n is the principal quantum number. The spatial dependence of the wave function of chemical bond electrons in a molecule $\psi_\alpha(1)$ /6/ is given by:

$$\psi_\alpha(1) = (1 + c_1 z_{\alpha 1})e^{-\alpha r_{ab}}$$

where $c_1$ is a variable parameter, $\alpha$ is the real attenuation constant, $r_{ab}$ is the distance between two atoms of a molecule, oriented along z axis. The emergence of electrical and magnetic moments by external electromagnetic field inducement is possible only in the case when conditions of spatial and time synchronism are satisfied. Synchronism is distinct from synchronization. Synchronization requires certain initial phase correlations between oscillations. On the other hand, synchronism means certain correlations between frequencies (time synchronism) or correlations between propagation constants of oscillations (spatial synchronism). These synchronism conditions are given as [7]:

$$\omega_1 + \omega_2 = \omega_3$$

$$\gamma_1 + \gamma_2 = \gamma_3$$

Where $\omega_1$, $\omega_2$, $\gamma_1$, $\gamma_2$ and $\omega_3$, $\gamma_3$ are frequencies and propagation constants of interacting and resultant waves respectively.

The propagation constant $\gamma$ is defined as [7]:

$$\gamma = \alpha + i\beta$$

Where $\alpha$ is the real attenuation constant and $\beta$ is the phase constant. The conditions of synchronism could be interpreted as lows of energy and momentum conservation at the process of interaction:

$$\hbar\omega_1 + \hbar\omega_2 = \hbar\omega_3$$

$$\hbar\gamma_1 + \hbar\gamma_2 = \hbar\gamma_3$$

The time dependence of the wave function of the electron in the atom is defined as $$\Psi_n(r,t) = \psi_n(r)e^{i\frac{E_n}{\hbar}t}.$$

Using the Einstein correlation $E=\hbar\omega$, the condition of time synchronism (or alternatively, the law of energy conservation) for the photon interaction the following results [3]:

$$i\hbar\frac{E_n}{\hbar} + i\hbar\omega = i\hbar\frac{E_m}{\hbar} \quad 1$$

$$E_m - E_n = \hbar\omega$$

Expression (1) is the principal condition for the stimulated emission or absorption of electromagnetic radiation to occur at the quantum transition of an electron from the state n into the state m. When $E_m > E_n$, the transition corresponds to the stimulated absorption. When $E_m < E_n$, the transition corresponds to stimulated emission. The spatial dependence of the wave function for the electrons of inner electron shells and chemical bonding electrons is expressed in the following form:

$$\psi(r) = \psi_0 e^{-\alpha r}$$

The conditions of spatial synchronism (or the law of conservation of momentum) can be written in the following form:

$$-\hbar\alpha_1 + \hbar\gamma = -\hbar\alpha_2$$

$$\gamma = (\alpha_1 - \alpha_2) \quad 2$$

On the right side of the expression (2) is a real quantity. Therefore, to excite chemical bonds, the propagation constant of vector potential $\vec{A}$ must generally be a real quantity as well. This requirement can be satisfied when the real part of the phase constant $\beta$ is equal to zero:

$$Im(\gamma) = 0 \rightarrow Re[\beta] = 0 \quad 3$$

If the propagation constant $\gamma$ is a complex quantity, then when $Re[\beta] >> \alpha$ the propagation of an electromagnetic field can be considered as propagation of a pulse filled up with the space-oscillating component of the field. Such a pulse can be considered to be a pulse with filling (video-pulse). If the propagation constant $\gamma$ is a real quantity ($Re[\beta]=0$), then there are no spatial oscillations, and electromagnetic field propagation could be represented in the form of propagation of the pulse without filling. This case corresponds to the propagation of a simple pulse with exponential attenuation. When combining (1), (2) and (3) to consider emergence of induced moments, it is helpful to use vector potential $\vec{A}$ which is an integral characteristic in relation to the electromagnetic field vectors $\vec{E}$ and $\vec{H}$, the vector potential $\vec{A}$ described below by:

$$\vec{A} = \vec{A}_0 e^{i\alpha r - \alpha r} \quad 4$$

Using the following expansion into the power series:

$$e^{-\alpha r} = 1 - \alpha r + 0[\alpha r]^2$$

expression (4) becomes the following:

$$\vec{A} = \vec{A}_0 e^{i\alpha r}(1 - \alpha r) \qquad 5$$

Expression (5) defines the form of vector potential $\vec{A}$ of electromagnetic fields needed to induce moments on the chemical bond electrons to result in excitation of the chemical bonds. Hence, in order to excite a chemical bond by an electromagnetic field, the vector potential $\vec{A}$ of the electromagnetic field should satisfy the following three (3) conditions which are satisfied by expression (5) above:

i) The vector potential must have oscillations (e.g. sinusoidal) in time;
 ii) The vector potential should not have spatial oscillations; and
 iii) The amplitude of the vector potential $\vec{A}$ must decrease linearly with distance.

The above vector potential $\vec{A}$ electromagnetic field requirements for producing inducedmoments on chemical bond electrons are extremely specific. At present, known electromagnetic fields may be classified into the following discrete groups:

i) electrostatic fields;
 ii) magnetostatic fields; and
 iii) electromagnetic fields with complex propagation constants.

Based on the requirements to excite a chemical bond by an electromagnetic field noted above, none of these field types can generally be used to excite chemical bonds. Electrostatic and magnetostatic fields do not cause the emergence of induced electric and magnetic moments on the chemical bond electrons because when these fields interact with matter the condition of time synchronism (1) is not satisfied. Electromagnetic fields with a complex propagation constant cannot cause the emergence of induced moments on chemical bond electrons because when such fields interact with matter the condition of spatial synchronism (2) is not satisfied.

In order to determine methods for production (formation) of electromagnetic fields having a vector potential, which satisfies condition (5), the propagation of the oscillations of vector potential $\vec{A}$ is considered. Generally propagation oscillations, such as oscillations of vector potential $\vec{A}$, is described by the Helmholtz wave equation which has the form of /8/:

$$\Delta f(x, y, z, t) = \frac{1}{a^2} \frac{\partial^2 f(x, y, z, t)}{\partial t^2} \qquad 6$$

Where $f(x, y, z, t)$ is a required function for oscillation and $\alpha$ is the phase speed of oscillations. The Laplacian operator in spherical system of coordinates has the following form:

$$\Delta = \frac{1}{r^2} \frac{\partial}{\partial r}\left(r^2 \frac{\partial}{\partial r}\right) + \frac{1}{r^2 \sin\theta} \frac{\partial}{\partial \theta}\left(\sin\theta \frac{\partial}{\partial \theta}\right) + \frac{1}{r^2 \sin^2\theta} \frac{\partial^2}{\partial \phi^2}$$

The angular part of Laplacian operator can be labeled with the symbol $\alpha_\otimes$:

$$\Delta_\otimes = \frac{1}{\sin\theta} \frac{\partial}{\partial \theta}\left(\sin\theta \frac{\partial}{\partial \theta}\right) + \frac{1}{\sin^2\theta} \frac{\partial^2}{\partial \phi^2}$$

Given that there is a harmonic dependence of the function on time $f = R(r)Y(\theta,\phi)e^{i\alpha r}$, equation (6) can be transformed into a system of two equations:

$$\Delta_\otimes Y + l(l+1)Y = 0 \qquad 6$$

Where l is an orbital quantum number.

$$\frac{1}{r^2} \frac{\partial}{\partial r}\left(r^2 \frac{\partial R}{\partial r}\right) + \left[k^2 - \frac{l(l+1)}{r^2}\right] R = 0 \qquad 6''$$

Where $k = \omega/\alpha$ is the wave number. The solutions of equation (6') are functions, which are called spherical harmonics $Y_l^m(\theta,\phi)$. The theory of these functions is described in [9]. Indices l and mn are members of a natural series, l being the orbital quantum number and mi being the azimuthal (magnetic) quantum number. Oscillations with l=0 are called zero-mode. Zero-mode is a defining mode for all wave processes. It can be considered as a first member of an expansion of the function of oscillations into a series. Zero-mode is often is called the energy mode or carrier mode. In quantum mechanics it corresponds to the 1s electron states. The importance of zero-mode is reflected in the fundamental constant considered to be the radius of the first Bohr orbit. In this particular case, function $f$ depends only from distance $r = \sqrt{x^2+y^2+z^2}$ and equation (6") can be written as:

$$\frac{1}{r} \frac{\partial}{\partial r}\left(r^2 \frac{\partial f}{\partial r}\right) = \frac{1}{a^2} \frac{\partial^2 f}{\partial t^2} \qquad 7$$

This well-known transformation can be used:

$$\frac{1}{r^2} \frac{\partial}{\partial r}\left(r^2 \frac{\partial f}{\partial r}\right) = \frac{\partial^2 f}{\partial r^2} + \frac{2}{r} \frac{\partial f}{\partial r} = \frac{1}{r} \frac{\partial^2 (rf)}{\partial r^2}$$

Then equation (7) may be written in the form of:

$$\frac{\partial (rf)}{\partial r^2} = \frac{1}{a^2} \frac{\partial^2 (rf)}{\partial t^2} \qquad 7'$$

A new function $u = rf$ can be defined and substituted it into expression (7'). This gives as a result the one-dimensional wave equation shown below:

$$\frac{\partial^2 u(r, t)}{\partial r^2} = \frac{1}{a^2} \frac{\partial^2 u(r, t)}{\partial t^2} \qquad 8$$

Equation (8) is called one-dimensional wave equation or equation for plane waves. This equation is one of hyperbolic type. Initial conditions that unambiguously define oscillations, which have the form of:

$$u\big|_{t=0} = f_0(r); \qquad \frac{\partial u}{\partial t}\bigg|_{t=0} = \psi(r) \qquad 8'$$

Problem (8), (8') is known as problem with initial conditions or Cauchy problem. The solution of this problem can be obtained using the method of D'Alembert [10]:

$$u(r, t) = \frac{f_0(r - at) + f_0(r + at)}{2} + \frac{1}{2a}\int_{r-at}^{r+at}\psi(r)dr \qquad 9$$

Expression (9) is called as formula of D'Alembert. It follows from formula (9) that the Cauchy problem (8), (8') for the wave equation has a single solution, which continuously depends on initial conditions. Solution (9) is valid, given that function $f_0(r)$ has derivatives up to the second order inclusive, and the function $\phi(r)$ has derivatives of first order. In the case when the function $\phi$ describes a wave subprocess with the same phase speed of propagation $\alpha$, then corresponding Cauchy problem may by written as:

$$\frac{\partial^2 \psi}{\partial r^2} = \frac{1}{a^2}\frac{\partial^2 \psi}{\partial t^2} \qquad 10$$

$$\psi|_{t=0} = f_1(r); \quad \left.\frac{\partial \psi}{\partial t}\right|_{t=0} = f_2(r) \qquad 10'$$

The solution of (10), (10') in accordance to the formula of D'Alembert (9) is:

$$\psi = \frac{f_1(r - at) + f_1(r + at)}{2} + \frac{1}{2a}\int_{r-at}^{r+at}f_2(r)dr \qquad 11$$

The function can be abbreviated as follows:

$$f(r \pm \alpha t) = f(r - \alpha t) + f(r + \alpha t)$$

Combining (9) and (11) the solution for the resultant oscillation is shown below:

$$u(r, t) = \qquad 12$$
$$\frac{1}{2}[f_0(r \pm at)] + \frac{1}{4a}\int_{r-at}^{r+at}f_1(r \pm at)dr + \frac{1}{4a^2}\int_{r-at}^{r+at}dr\int_{r-at}^{r+at}f_2(r)dr$$

In accordance with the initial conditions (8') and (10') the expression (12) may be written in the following form:

$$u = \frac{u|_{t=0}}{2} + \frac{1}{4a}\int_{r-at}^{r+at}\left.\frac{\partial u}{\partial t}\right|_{t=0}dr + \frac{1}{4a^2}\int_{r-at}^{r+at}dr\int_{r-at}^{r+at}\left.\frac{\partial^2 u}{\partial t^2}\right|_{t=0}dr \qquad 13$$

Or through directional derivatives:

$$u = \frac{u|_{t=0}}{2} + \frac{1}{4}\int_{r-at}^{r+at}u'\bigg|_{t=0}dr + \frac{1}{4}\int_{r-at}^{r+at}dr\int_{r-at}^{r+at}u''\bigg|_{t=0}dr \qquad 13'$$

The solution of D'Alembert (13') for the wave of vector potential has a form of:

$$\vec{A} = \vec{A}\bigg|_{t=0} + \frac{1}{4}\int \vec{A}'\bigg|_{t=0}dr + \frac{1}{4}\int dr\int \vec{A}''\bigg|_{t=0}dr \qquad 14$$

In the international system of units (SI) vector potential $\vec{A}$ and scalar potential $\phi$ may be expressed through the magnetic induction $\vec{B}$ and the strength of electric field $\vec{E}$ as follows:

$$\vec{E} = -\frac{\partial \vec{A}}{\partial t} - \vec{\nabla}\varphi \qquad \vec{B} = \vec{\nabla} \times \vec{A} \qquad 15$$

Magnetic induction $\vec{B}$ and strength of electric field $\vec{E}$ are connected by Maxwell's equations, which in the international system of units (SI) have the form of [7]:

$$\vec{\nabla} \times \vec{E} = -\frac{\partial \vec{B}}{\partial t} \qquad 16$$

$$\vec{\nabla} \times \vec{H} = \vec{j}_c \frac{\partial \vec{D}}{\partial t} \qquad 16'$$

Where E, H are strength of electric field and strength of magnetic field vectors, respectively; $\vec{D}$ and $\vec{B}$ are vectors of electric and magnetic induction, respectively and $\vec{j}_c$ is the current density. Respective strength vectors are related to respective induction vectors as follows:

$$\vec{D} = \epsilon\epsilon_0 \vec{E} \quad \vec{B} = \mu\mu_0 \vec{H} \qquad 17$$

Where $\epsilon, \mu$ are the electric permittivity and magnetic permeability respectively; $\epsilon_0, \mu_0$ are the electric and magnetic permittivity constant of free space, respectively, in SI units. The electric and magnetic permittivity constants are related to each other through the speed of light c:

$$c^{-2} = \mu_0 \epsilon_0$$

By the substitution of (17) into equation (16') the following equation results:

$$\vec{\nabla} \times \vec{B} = \frac{1}{a^2}\frac{\partial \vec{E}}{\partial t} + \mu\mu_0 \vec{j}_c \qquad 18$$

Where $\alpha = c/\sqrt{\epsilon\mu}$—phase speed of the wave of vector potential $\vec{A}$ (system SI). Substituting (15) into equation (18) the following equation results:

$$\vec{\nabla} \times (\vec{\nabla} \times \vec{A}) = -\frac{1}{a^2}\frac{\partial^2 \vec{A}}{\partial t^2} - \frac{1}{a^2}\frac{\partial(\vec{\nabla}\varphi)}{\partial t} + \mu\mu_0 \vec{j}_c \qquad 19$$

However, it can be shown that $\vec{\nabla} \times (\vec{\nabla} \times \vec{A}) = -\vec{A}''$.

Theorem

For the arbitrary complex function $f$, the spatial dependence of which is assigned by the radius-vector $\vec{r}$, the identity $\vec{\nabla} \times (\vec{\nabla} \times \vec{f}) = -\vec{f}''$ is always valid. See the Appendix for the proof of this relation, which includes equations 20–29.

Using $$\vec{\nabla} \times (\vec{\nabla} \times \vec{A}) = -\frac{1}{a^2}\frac{\partial^2 \vec{A}}{\partial t^2},$$

from (19) the following is obtained:

$$\frac{1}{a^2}\frac{\partial}{\partial t}\left(\vec{\nabla}\varphi - \frac{\partial \vec{A}}{\partial t}\right) = -\frac{1}{a^2}\frac{\partial^2 \vec{A}}{\partial t^2} + \mu\mu_0 \vec{j}_c \qquad 29$$

Assuming that at an initial moment of time t=0, the separation constant for the equation (29) is equal to zero, a system of two equations can be obtained:

$$\frac{1}{a^2}\frac{\partial}{\partial t}\left(\vec{\nabla}\varphi - \frac{\partial \vec{A}}{\partial t}\right)\bigg|_{t=0} = 0 \qquad 30$$

$$-\frac{1}{a^2}\frac{\partial^2 \vec{A}}{\partial t^2} + \mu\mu_0 \vec{j}_c\bigg|_{t=0} = 0$$

From (30) follows:

$$\frac{\partial \vec{A}}{\partial t}\bigg|_{t=0} = \vec{\nabla}\varphi \quad \left(\vec{A}'' \equiv \frac{1}{a^2}\frac{\partial^2 \vec{A}}{\partial t^2}\right)\bigg|_{t=0} = \mu\mu_0 \vec{j}_c \qquad 31$$

By the substitution of (31) into (14) we obtain solution of D'Alembert for the wave of vector potential in homogenous media with the constants $\epsilon$ and $\mu$:

$$\vec{A} = \vec{A}_0 + \frac{\sqrt{\varepsilon\mu}}{4c}\int_{r-at}^{r+at}\vec{\nabla}\varphi\, dr + \frac{\mu\mu_0}{4}\int_{r-at}^{r+at} dr \int_{r-at}^{r+at}\vec{j}_c dr \qquad 32$$

Given that variations of electric current density is notrelated with variations of scalar potential, two non-synchronized branches of oscillations using Lorentz gauge relation can be obtained [7; 10]:

$$(\vec{\nabla}, \vec{A}) + \frac{1}{a^2}\frac{\partial \varphi}{\partial t} = 0$$

Corresponding non-synchronized oscillations will have the form of:

$$\Delta\varphi - \frac{1}{a^2}\frac{\partial^2 \varphi}{\partial t^2} = -\frac{\rho}{\varepsilon\varepsilon_0} \quad \Delta\vec{A} - \frac{1}{a^2}\frac{\partial^2 \vec{A}}{\partial t^2} = -\mu\mu_0 \vec{j}_c$$

In accordance with Ohm's law, in systems with finite conductivity variation of electrical current is followed by a corresponding variation in voltage. As a result variations of the electrical current density ($\vec{j}_c$) can be connected with variations of the gradient of scalar potential. These variations can be synchronized; Correspondingly, synchronization of changes can be organized as time synchronization or as time-spatial synchronization. In accordance with (8) and (10), the wave of vector potential (32) may be represented in the form of complex oscillation. The main (principal) branch of oscillations (carrier) is defined by the following equation:

$$\frac{\partial^2 \vec{A}}{\partial r^2} = \frac{1}{a^2}\frac{\partial^2 \vec{A}}{\partial t^2} \quad \vec{A}\bigg|_{t=0} = \vec{A}_0, \quad \frac{\partial \vec{A}}{\partial t}\bigg|_{t=0} = \vec{\nabla}\varphi \qquad 33$$

The secondary branch of oscillations (sub-carrier) is defined by the equations:

$$\frac{\partial^2(\vec{\nabla}\varphi)}{\partial r^2} = \frac{1}{a^2}\frac{\partial^2(\vec{\nabla}\varphi)}{\partial t^2} \qquad 34$$

$$(\vec{\nabla}\varphi)\bigg|_{t=0} = (\vec{\nabla}\varphi)_0, \quad \frac{\partial(\vec{\nabla}\varphi)}{\partial t}\bigg|_{t=0} = a^2\mu\mu_0 \vec{j}_c$$

In the Cauchy problems (33) and (34) condition for time synchronization is:

$$\frac{\partial \vec{A}}{\partial t}\bigg|_{t=0} = \vec{\nabla}\varphi \quad \frac{\partial(\vec{\nabla}\varphi)}{\partial t}\bigg|_{t=0} = a^2\mu\mu_0 \vec{j}_c \qquad 35$$

Equation 35 is a condition of time synchronization. It shows that variation of the vector potential $\vec{A}$ in time must be synchronized with variation of a scalar potential in time. In this case, both processes must happen simultaneously during a certain time, called the synchronization time. Thus, synchronization expressed by equation 35 requires correlation between initial phases of vector and scalar potential. Synchronism, on the other hand, refers to correlation between frequencies or propagation constants.

In order to achieve time synchronization, the function of the gradient of the scalar potential $\vec{\nabla}\phi$ must have time derivatives of the first and second orders, and a function of the electric current density $\vec{j}_c$ must have time derivatives of the first order. This will correspond to the case of the systems with concentrated (as opposed to distributed) parameters due to the fact that the above requirements for the directional derivatives are not defined.

In order to achieve conditions of spatial-time synchronization between branches (33) and (34) it is required that the gradient of scalar potential $\vec{\nabla}\phi$ must have directional derivatives of the first and second order and function of the electric current density $\vec{j}_c$ must have a defined directional derivative of the first order. This will correspond to systems having distributed parameters because of the well-defined directional derivatives provided by such systems.

In correspondence to the Cauchy conditions, the oscillating process (34) is defined, provided the electric current density $\vec{j}_c$ directional derivative of the first order $$\vec{j}'_c \equiv \frac{\partial \vec{j}_c}{\partial r}$$

exists. In accordance with (31), this requirement corresponds to the requirement of existence of directional derivative of the third order $\vec{A}'''$.

Therefore condition (14) is valid only in the case when directional derivatives of the first, second and third order for the vector potential are defined:

$$\vec{A}' \equiv \frac{\partial \vec{A}}{\partial r} \quad \vec{A}'' \equiv \frac{\partial^2 \vec{A}}{\partial r^2} \quad \vec{A}''' \equiv \frac{\partial^3 \vec{A}}{\partial r^3} \qquad 36$$

In general case $\epsilon$ and $\mu$ may depend on the direction of the field propagation. Therefore for the systems with variable $\epsilon$ and $\mu$ from (31) the following applies:

$$\vec{A}'' = \frac{\partial}{\partial r}\left(\frac{\sqrt{\epsilon\mu}}{c}\vec{\nabla}\varphi\right) = \frac{\sqrt{\epsilon\mu}}{c}\left\{\frac{\vec{\nabla}\varphi}{2}\left(\frac{\mu'}{\mu} + \frac{\epsilon'}{\epsilon}\right) + (\vec{\nabla}\varphi)'\right\} \qquad 37$$

$$\vec{A}'' = \mu\mu_0 \vec{j}_c$$

Where $\mu' = \partial\mu/\partial r$, $\epsilon' = \partial\epsilon/\partial r$.

From (37) we obtain a differential analog, which is closely related to the parameters recited in Ohm's law:

$$\frac{\vec{\nabla}\varphi}{2}\left(\frac{\mu'}{\mu} + \frac{\epsilon'}{\epsilon}\right) + (\vec{\nabla}\varphi)' = Z_0 \vec{j}_c \qquad 38$$

Where $$Z_0 = \sqrt{\frac{\mu\mu_0}{\epsilon\epsilon_0}}$$

is the characteristic impedance of the medium. It follows from (38) that $\vec{j}_c$ is determined by two components. The first component is the gradient of scalar potential $\vec{\nabla}\phi$ multiplied by the sum of relative changes of magnetic permeability and electric permittivity. The second component is defined by the speed of change of the gradient $$(\vec{\nabla}\varphi)' \equiv \frac{\partial}{\partial r}\vec{\nabla}\varphi$$

along the selected direction r. Electric permittivity and magnetic permeability define electric and magnetic losses in matter as well as the related processes of relaxation during the action of electromagnetic fields on the matter. Correspondently the changes in electric permittivity and magnetic permeability are defined by the mechanism of polarization and magnetization of matter. Therefore the first component in (38) can be seen to be responsible for the active (Ohmic) and reactive losses. From (37) the directional derivative of the third order $\vec{A}'''$ is as follows:

$$\vec{A}''' = \frac{\sqrt{\epsilon\mu}}{c} \qquad 39$$

$$\left\{(\vec{\nabla}\varphi)'\left(\frac{\mu'}{\mu} + \frac{\epsilon'}{\epsilon}\right) + (\vec{\nabla}\varphi)'' + \frac{\vec{\nabla}\varphi}{2}\left(\frac{\mu''}{\mu} + \frac{\epsilon''}{\epsilon}\right) - \frac{\vec{\nabla}\varphi}{4}\left(\frac{\mu'}{\mu} - \frac{\epsilon'}{\epsilon}\right)^2\right\}$$

$$\vec{A}''' = \mu'\mu_0 \vec{j}_c + \mu\mu_0 \vec{j}_c'$$

It follows from (39) that relation (14) is valid if the direction of $$\vec{\nabla}\varphi, \text{ or } \frac{\partial}{\partial r}\vec{\nabla}\varphi,$$

or $$\frac{\partial^2}{\partial r^2}\vec{\nabla}\varphi$$

is defined, or the spatial structure of $\epsilon$ and $\mu$ is defined. Therefore, waves of vector potential satisfying (14) could be formed only when the electromagnetic fields have a defined spatial structure. The spatial structure of an electromagnetic field is called its mode [7]. Generation of electromagnetic fields having waves of vector potential satisfying (14) can be provided by distributed oscillation systems, such as cavity resonators, open (optical) resonators or waveguide systems including radio waveguides.

To find the additional conditions needed to form electromagnetic fields with defined waves of the vector potential $\vec{A}$ satisfying equation (14), the reaction of the wave contributions (components) $\vec{A}_1 = \int \vec{A}' dr$ and $\vec{A}_2 = \int dr \int \vec{A}''$ on the various test functions were investigated. The following functions were considered:

1. Sine wave oscillations $f = \sin[kr]$.
2. Exponentially damped oscillations $f = e^{-\alpha r} \sin[kr]$.
3. Slow damped oscillations $$f = \frac{\sin[kr]}{\pi r}.$$

4. Fast damped oscillations $$f = \frac{ke^{-ikr}}{\pi(k^2 r^2 + 1)}.$$

For the test, it was assumed that: $a = 3 \times 10^8$ m/s and $\lambda = 60$ cm (frequency 500 MHz), synchronization time $t = 10^{-8}$ c, attenuation constant $\alpha = 1$. The limits of integration chosen were symmetrical. The upper limit used was r+at and the lower limit used was r−at. In the case of symmetrical limits of integration, the value of the integral from harmonic oscillations of the type $e^{-ikr}$ and from sine wave oscillations are always equal to zero as shown below:

$$A_1 = \int_{r-at}^{r+at} \sin[kr] dr = 0 \qquad 40$$

$$A_2 = \int_{r-at}^{r+at} dr \int_{r-at}^{r+at} \sin[kr] dr = 0$$

It follows from (40), that harmonic oscillations of types $\sin[kr]$ and $\cos[kr]$, or in the general case of type $e^{-ikr}$ produce zero contributions in the wave of vector potential. Therefore, harmonic oscillations cannot generally be used to generate an electromagnetic field with a defined vector potential wave, which satisfies equation (14).

Figure 1:
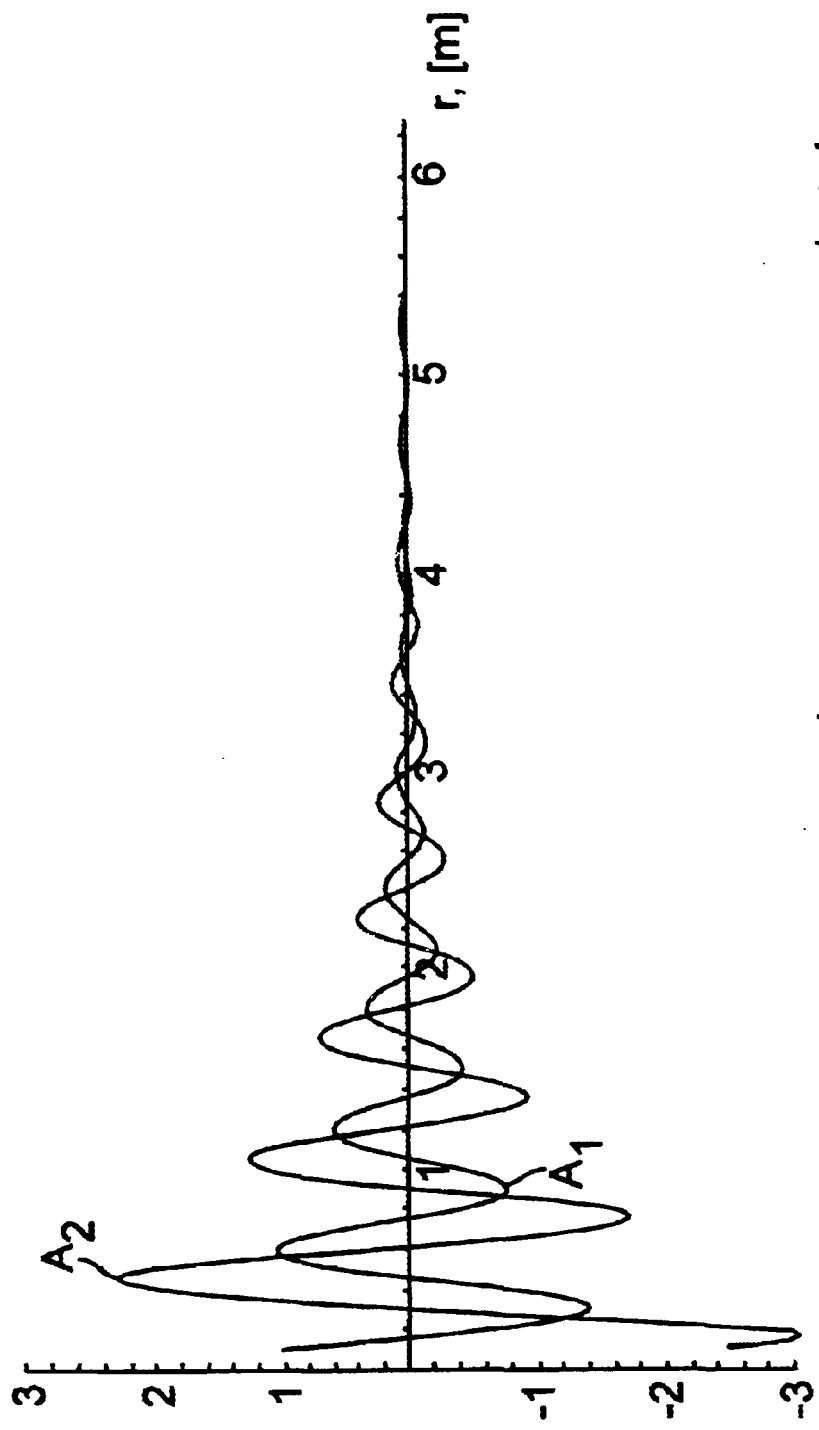
FIG. 1 illustrates graphs of the functions $$A_1 = \int_{r-at}^{r+at} e^{-ar}\sin[kr]\,dr \quad \text{and} \quad A_2 = \int_{r-at}^{r+at} dr \int_{r-at}^{r+at} e^{-ar}\sin[kr]\,dr.$$

Graphs $$A_1 = \int_{r-at}^{r+at} e^{-\alpha r} \sin[kr] dr \quad \text{and}$$

$$A_2 = \int_{r-at}^{r+at} dr \int_{r-at}^{r+at} e^{-\alpha r} \sin[kr] dr$$

are shown in FIG. 1. Exponentially damped oscillations, such as those shown above, are invariant to the operations of differentiation and integration. The form of these functions is preserved under these operations and only the amplitude and phase of the function can be changed.

In accordance with (5), in order to produce the emergence of induced moments on bonding electrons the applied electromagnetic field must have a vector potential $\vec{A}$ in the form of:

$$\vec{A} = \vec{A}_0 (1 - \alpha r) \qquad 41$$

As noted earlier, the functions $A_1$ and $A_2$ (see FIG. 1) or more generally, exponentially damped oscillations of type $e^{-\alpha r} \sin[kr]$, or functions of type $e^{-\alpha r} e^{-ikr}$ cannot be used to generate vector potential in the form of (41). Therefore, this type of oscillation is not useful to produce the excitation of a chemical bond by the action of an electromagnetic field.

Figure 2:
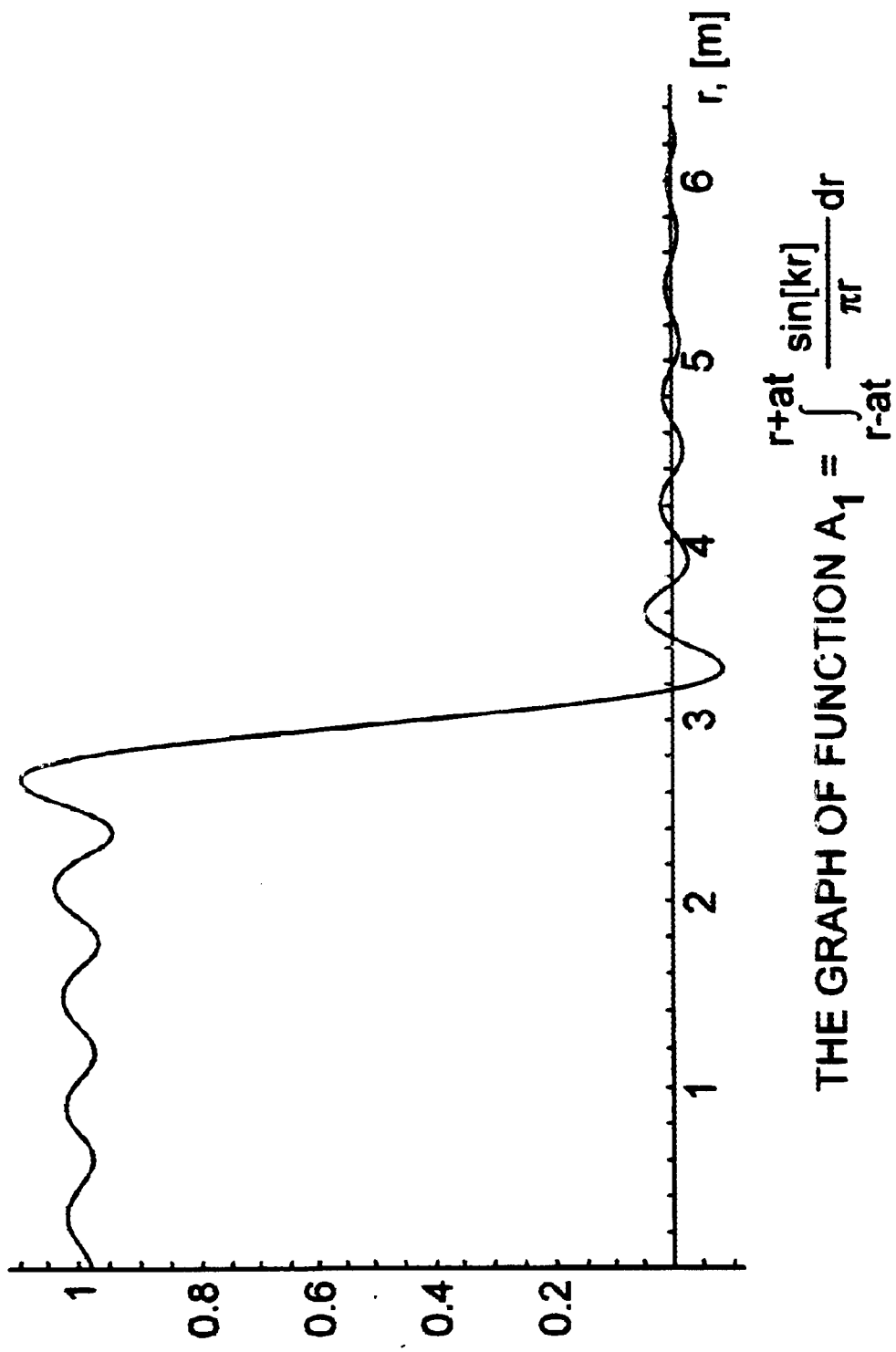
FIG. 2 illustrates a graph of $$A_1 = \int_{r-at}^{r+at} \frac{\sin[kr]}{\pi r}\,dr.$$

However, oscillations of the type $$f = \frac{\sin[kr]}{\pi r}$$

damp slower than oscillations of type $e^{-\alpha r} \sin[kr]$. A Graph of $$A_1 = \int_{r-at}^{r+at} \frac{\sin[kr]}{\pi r} dr$$

is shown in FIG. 2. As shown in FIG. 2, in the region r<at, function $A_1$ is close to a constant value, approximately equal to 1. In the proximity of the region where r=at, a sharp decrease in the $A_1$ value occurs. In the area of r>at, the function $A_1$ is seen to damp in amplitude in proportion to 1/r.

Figure 3:
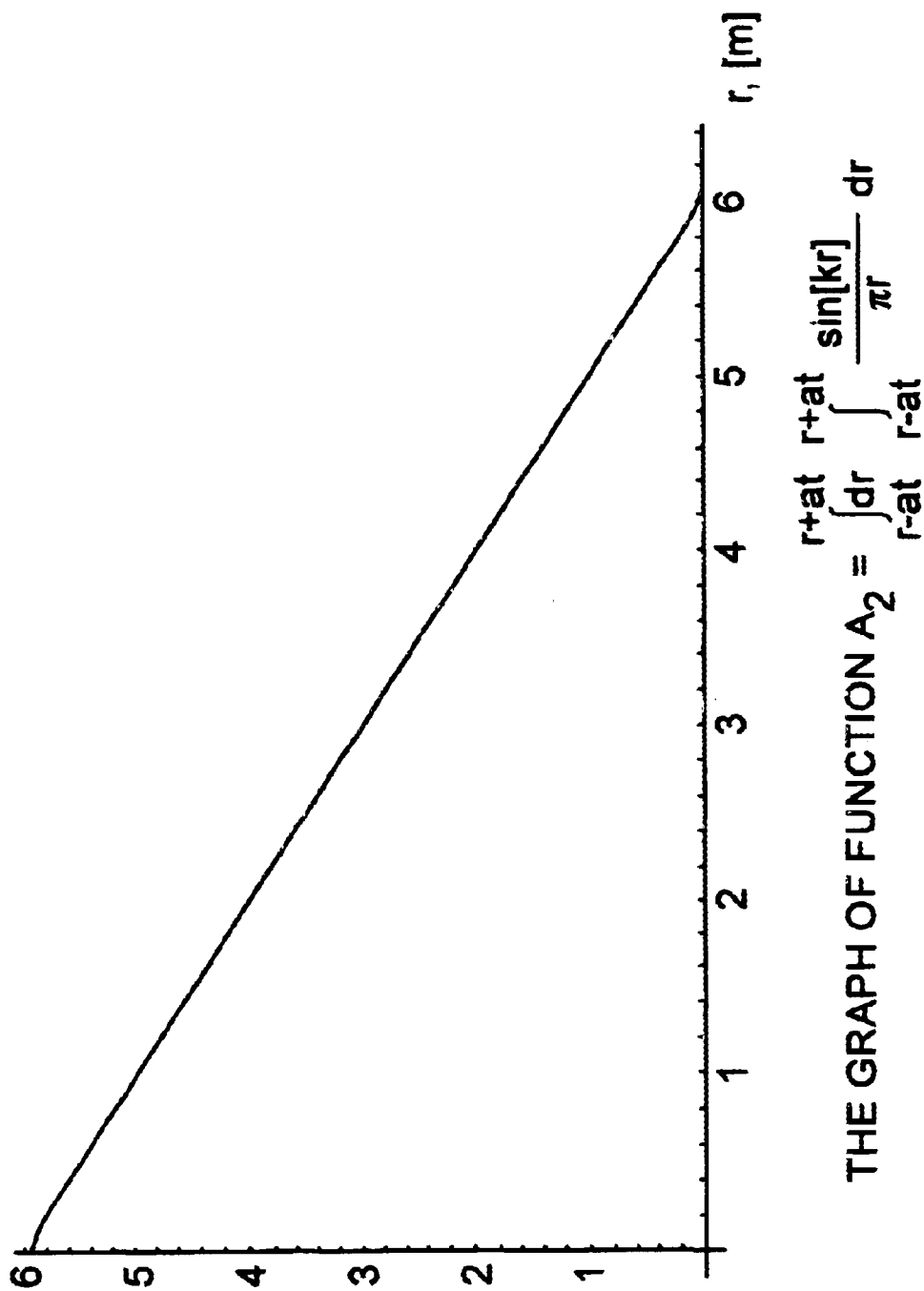
FIG. 3 illustrates a graph of $$A_2 = \int_{r-at}^{r+at} dr \int_{r-at}^{r+at} \frac{\sin[kr]}{\pi r} dr.$$

A graph of $$A_2 = \int_{r-at}^{r+at} dr \int_{r-at}^{r+at} \frac{\sin[kr]}{\pi r} dr$$

is shown in the FIG. 3. In the area of $r \leq 2at$ function $A_2$ is linear and decreasing as the function $$2at\left(1 - \frac{r}{2at}\right).$$

In the area of r>2at function $A_2$ is damping in proportion to 1/r (small amplitude oscillations with the amplitude decreasing as 1/r). Therefore, $A_2$ satisfies to the condition (41) in the area of $r \leq 2at$. The real attenuation constant $\alpha$ in this case is equal to:

$$\alpha = \frac{1}{2at}$$

Hence, chemical bonds can be excited by an electromagnetic field with a vector potential $\vec{A}$ having wave component $A_2$ which has oscillations that damp slower than exponential oscillations of type $e^{-\alpha r} e^{-ikr}$. Excitation of the chemical bonds occurs as a result of the emergence of the induced moments on the electrons that constitute the chemical bond.

Figure 4:
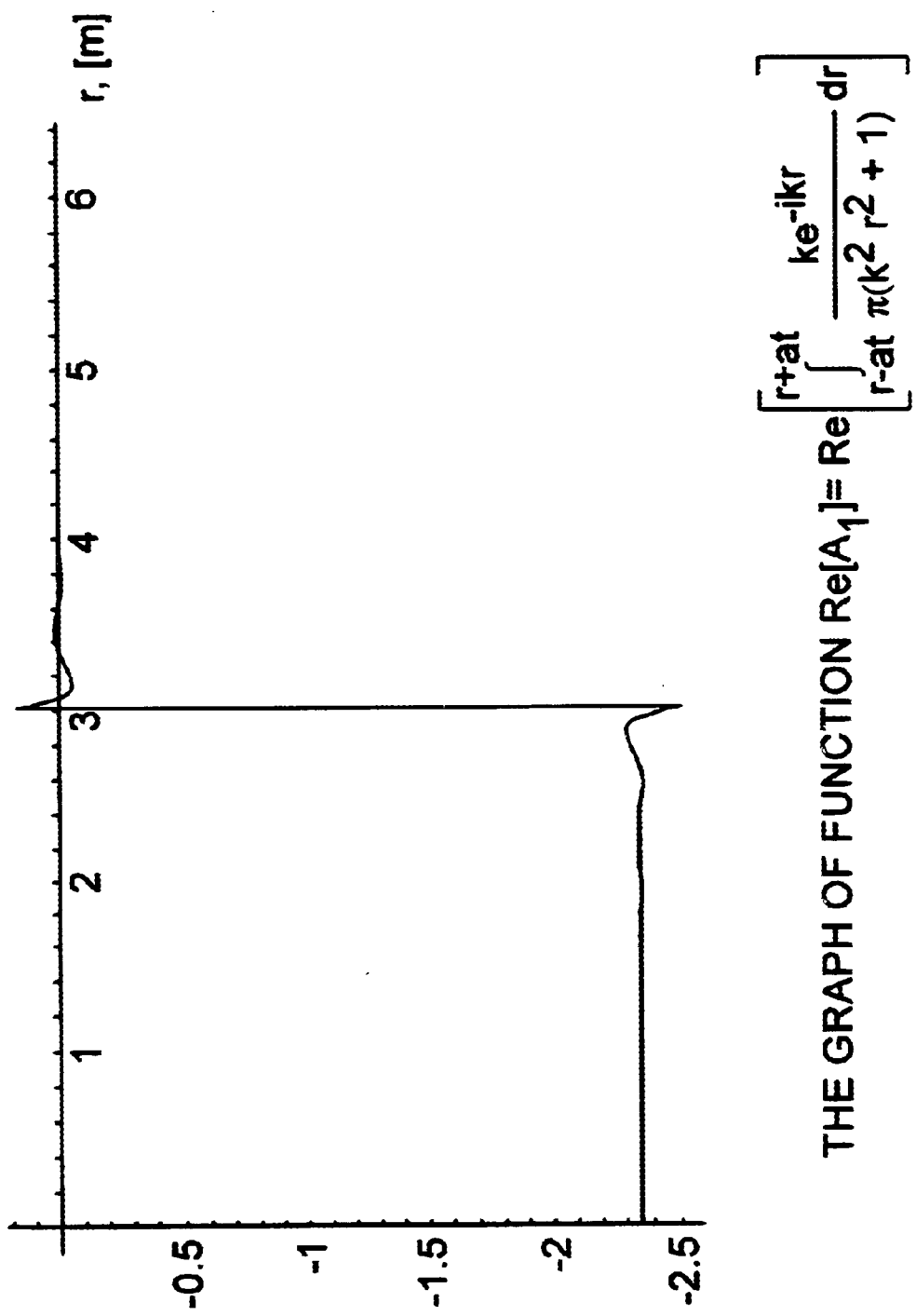
FIG. 4 illustrates the real part of the function $$\text{Re}[A_1] = \text{Re}\left[\int_{r-at}^{r+at} \frac{ke^{-ikr}}{\pi(k^2r^2+1)} dr\right].$$

Oscillations of $$f = \frac{ke^{-ikr}}{\pi(k^2 r^2 + 1)}$$

are damping faster than oscillations of type $e^{-\alpha r} e^{-ikr}$. A graph of the real part of the function $$\text{Re}[A_1] = \text{Re}\left[\int_{r-at}^{r+at} \frac{ke^{-ikr}}{\pi(k^2 r^2 + 1)} dr\right]$$

is shown in FIG. 4. When r<at, the function $\text{Re}[A_1]$ is close to a constant value, equal to approximately 2.35. Near r~at, a sharp decrease in the value $\text{Re}[A_1]$ occurs. In the range of r>at, the function $\text{Re}[A_1]$ damps as function of $1/r^2$.

Figure 5:
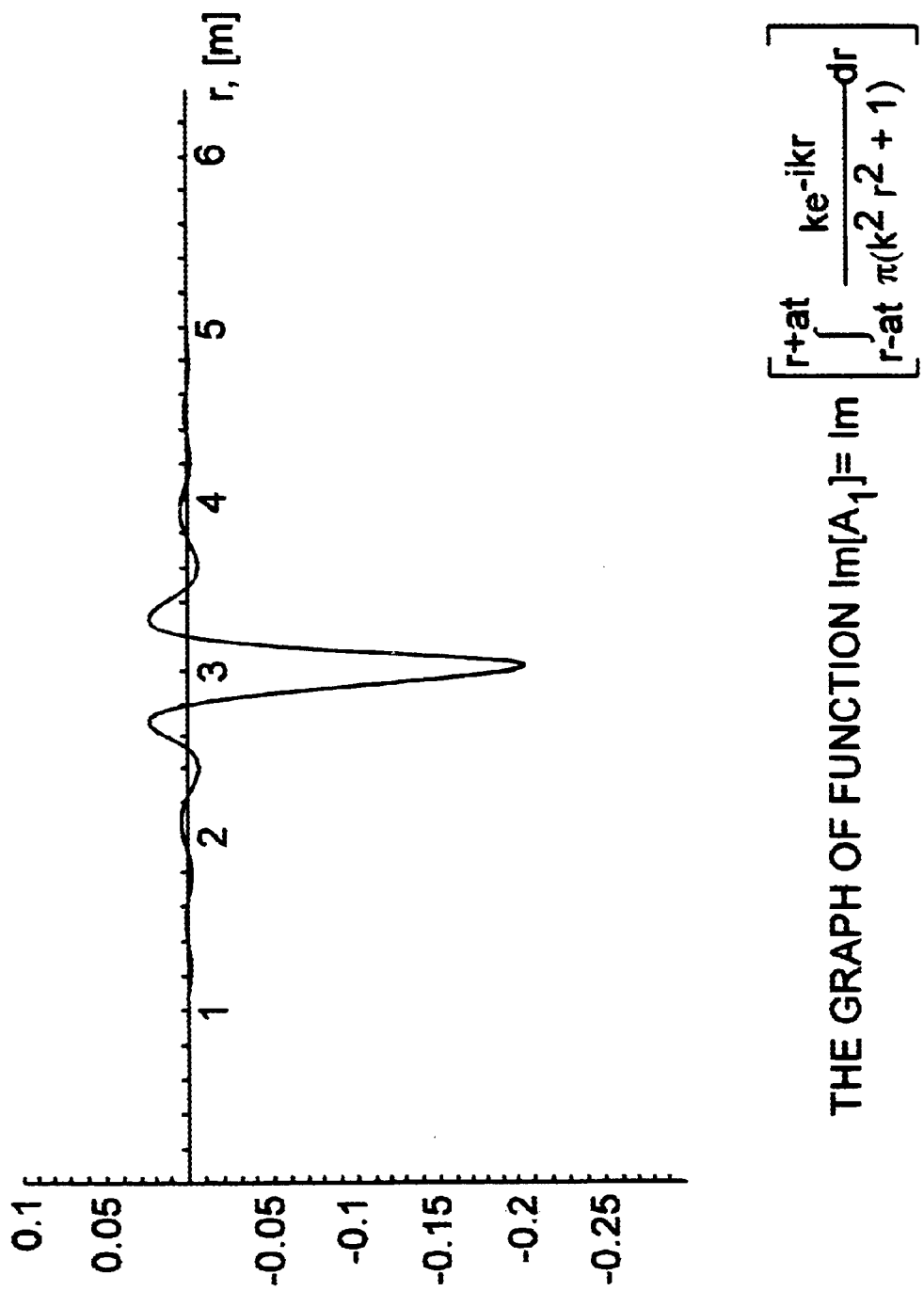
FIG. 5 illustrates the imaginary part of the function $$\text{Im}[A_1] = \text{Im}\left[\int_{r-at}^{r+at} \frac{ke^{-ikr}}{\pi(k^2r^2+1)} dr\right].$$

A graph of the imaginary part of the function $$\text{Im}[A_1] = \text{Im}\left[\int_{r-at}^{r+at} \frac{ke^{-ikr}}{\pi(k^2 r^2 + 1)} dr\right]$$

is shown in FIG. 5. The function shown is close to zero at any nearly all values of r. There is a singularity shown near r~at, where there is a local minimum with a value equal to approximately −0.20579.

Figure 6:
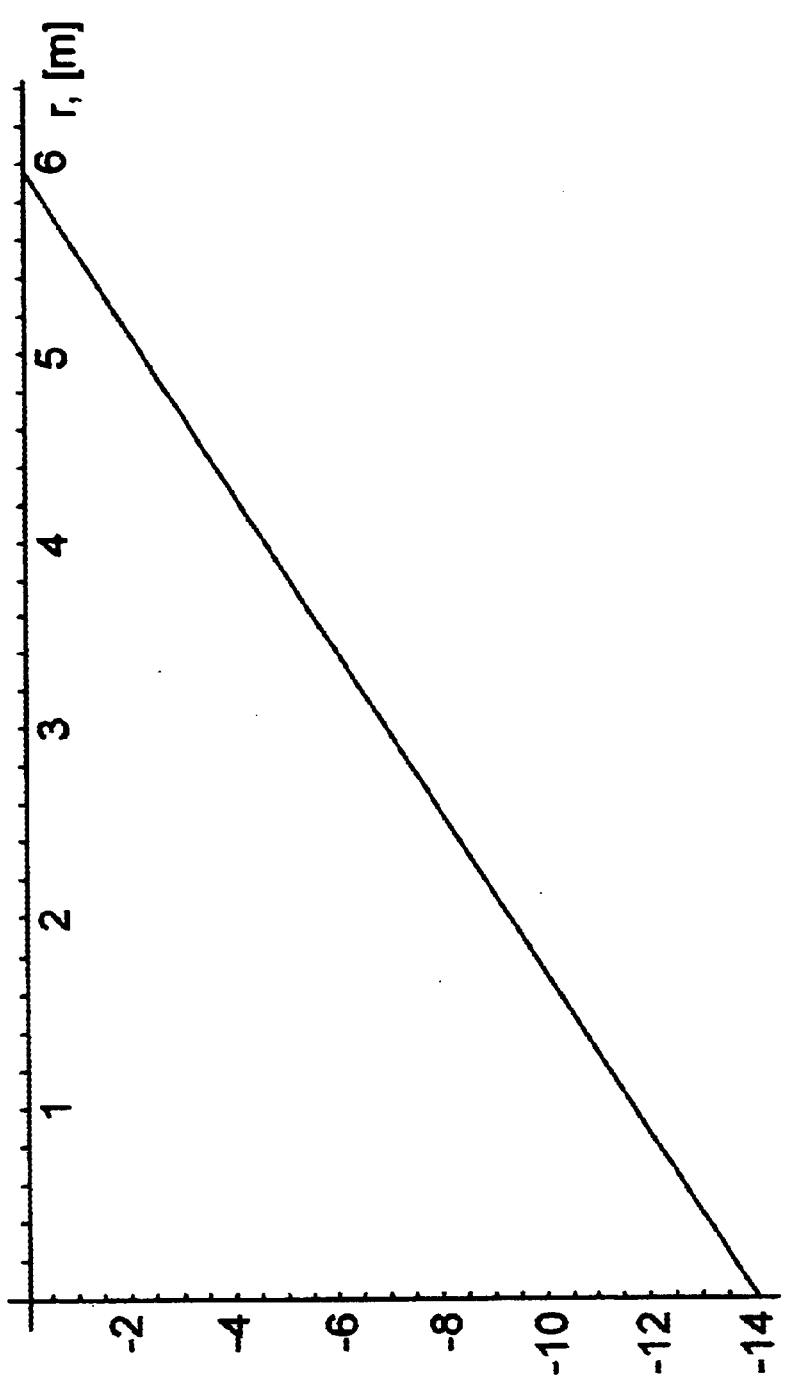
FIG. 6 illustrates a graph of $$\text{Re}[A_2] = \text{Re}\left[\int_{r-at}^{r+at} dr \int_{r-at}^{r+at} \frac{ke^{-ikr}}{\pi(k^2r^2+1)} dr\right].$$

A graph of $$\text{Re}[A_2] = \text{Re}\left[\int_{r-at}^{r+at} dr \int_{r-at}^{r+at} \frac{ke^{-ikr}}{\pi(k^2 r^2 + 1)} dr\right]$$

is shown in FIG. 6. In the range of $r \leq 2at$ function $\text{Re}[A_2]$ is linear and decreasing as $$-2.35\left(2at\left(-1\frac{r}{2at}\right)\right)$$

Figure 7:
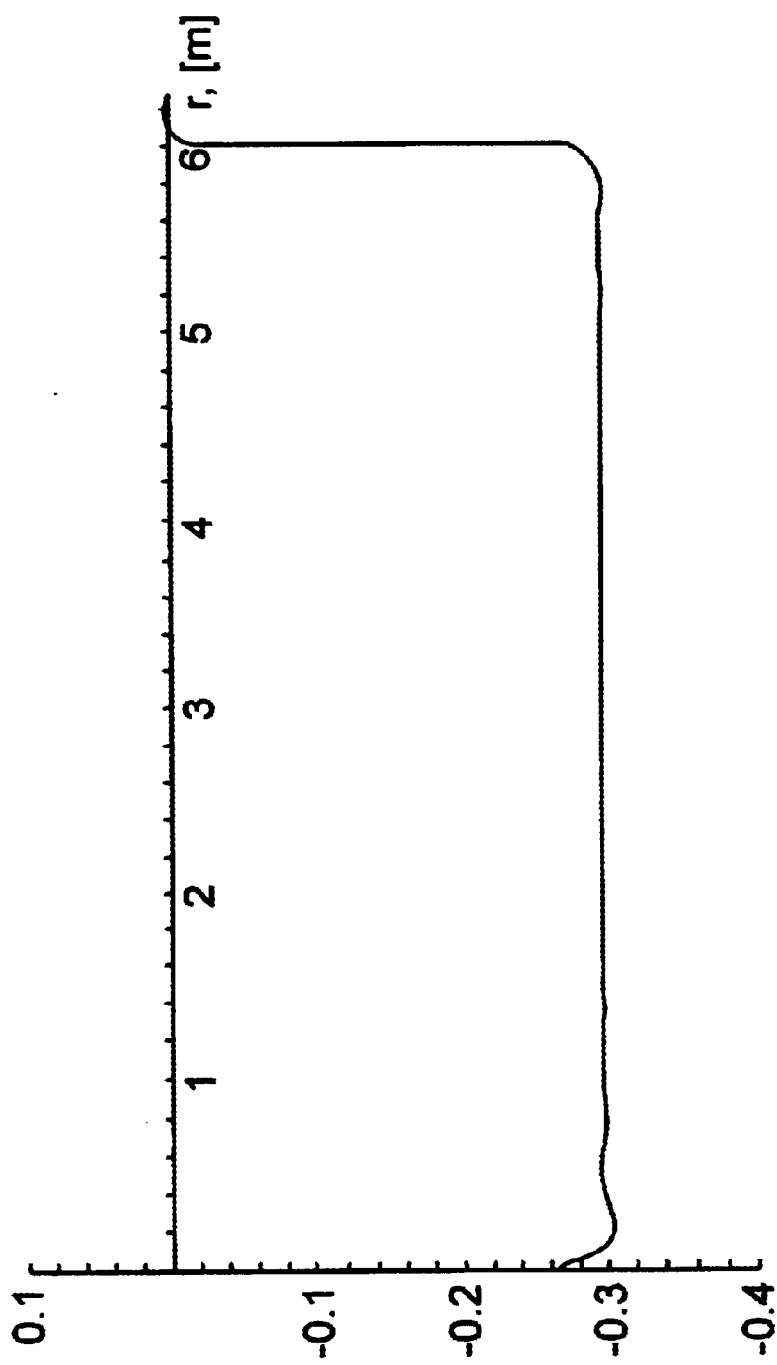
FIG. 7 illustrates a graph of the imaginary part $$\text{Im}[A_2] = \text{Im}\left[\int_{r-at}^{r+at} dr \int_{r-at}^{r+at} \frac{ke^{-ikr}}{\pi(k^2r^2+1)} dr\right].$$

In the range of r>2at $\text{Re}[A_2]$ damps according to $1/r^2$. A graph of the Imaginary part $$\text{Im}[A_2] = \text{Im}\left[\int_{r-at}^{r+at} dr \int_{r-at}^{r+at} \frac{ke^{-ikr}}{\pi(k^2 r^2 + 1)} dr\right]$$

is shown in FIG. 7.

When r<2a, the function $\text{Im}[A_2]$ has small amplitude of oscillation and is close to the constant value, equal to approximately 0.295. Near r~2at, the value of $\text{Im}[A_2]$ sharply decreases. In the range of r>2at, the function $\text{Im}[A_2]$ damps as $1/r^2$. The function $\text{Re}[A_2]$ shown in FIG. 6 satisfies condition (41) in the range of $r \leq 2at$. In this case the real attenuation constant $\alpha$ is equal to:

$$\alpha = \frac{1}{2at}$$

Therefore, chemical bonds can be excited by an electromagnetic field with a wave of the vector potential $\vec{A}$ having wave component $A_2$, because oscillations produced by $A_2$ damp faster than exponential oscillations of type $e^{-\alpha r} e^{-ikr}$. Thus, in order to produce excitation of bonding electrons, the wave component of vector potential $\vec{A}_2 = \int dr \int \vec{A}'' dr$ oscillations provided must damp either faster or slower, but not equal to exponential oscillations of type $e^{-\alpha r} e^{-ikr}$. Electromagnetic fields with waves of vector potential $\vec{A}$ formed by oscillations of type $e^{-\alpha r} e^{-ikr}$ not produce excitation of chemical bonds. Harmonic oscillations of type $e^{-ikr}$ give zero contribution in the wave of vector potential and in this sense cannot excite chemical bonds. Arbitrary oscillation systems with a single oscillation mode are always characterized by having exponential damping in the form of $e^{-\alpha r} e^{-ikr}$. These oscillation systems, which necessarily produce a single oscillation mode, are not useful for exciting chemical bonds.

In order to obtain a speed of damping of oscillations other than the exponent type $e^{-\alpha r}e^{-ikr}$, self-sustained oscillation systems, which can simultaneously support several oscillation modes, are preferably used. A self-sustained oscillation system is a system that generates oscillations, which once begun, do not require external application of force to sustain the oscillations. These self sustained oscillation systems which support several oscillation modes are referred to herein as being capable of operating in the "concurrence of modes" condition.

In concurrence of modes condition, which is present when different modes of oscillations are simultaneously present in the system, the suppression of certain modes by the other modes can occur. One rising mode can lead to additional nonlinear damping of other oscillatory modes present. As a result of this inter-mode interaction, the function describing the speed of damping of oscillations becomes different from exponential one of type $e^{-\alpha r}e^{-ikr}$. Damping may occur faster or slower than the exponential one ($e^{-\alpha r}e^{-ikr}$), in the cases of rising of a selected mode or suppression of the selected mode, respectively.

The concurrence of mode condition is generally only possible if all modes receive energy from the same energy source. A simple combination of generators with separate power supplies will not generally provide a concurrence of modes condition due to separation of sources of energy because the main reason for changes in damping rates being different from exponential is transfer of energy between concurrent modes. The combination of oscillation modes from a plurality of systems having different sources of energy will give only the mixture of oscillations, but will not result in concurrence of modes operation. Therefore, multimode operation is possible only in the case when there is a single common source of energy.

As noted earlier, a self-sustained oscillation system with distributed parameters is needed. For example, such a system can preferably be a cavity resonator with a discrete spectrum of proper frequencies. Even with a self-sustained oscillation system with distributed parameters, mode coupling must be kept weak to support the concurrence of mode condition.

In the case of a weak coupling between a plurality of self-sustained oscillation modes, these modes can coexist without suppressing each other. However, if the coupling is too strong, then only one mode will survive and dominate. To distinguish strong and weak coupling, it is helpful to consider the spectral characteristics of two different modes relating to their functional dependence between amplitude and frequency of oscillation. In the case where these characteristics are overlapping on the level, which is laying lower than half-width of spectral line, it corresponds to a weak coupling between modes. In the case where the spectral lines are overlapping on the level, which is laying higher than half-width, it corresponds to the strong coupling between modes.

Generally, any electrical or magnetic circuit with distributed parameters can be a multimode self-sustained oscillation system. This is best illustrated by the extracts from a textbook on the theoretical basics of electrical engineering [11].

By definition, electrical lines with distributed parameters are lines, where at the same moment of time, the current and voltage are different and continuously changing at any two neighboring points (cross-sections) of the line, so that they are functions of time and spatial coordinates. From the mathematical point of view such a system is a system having non-zero derivatives of current and voltage, with respect to either time or space, or both.

Magnetic lines with distributed parameters are lines, where the magnetic flux and magnetic difference of potentials are different and continuously change at any two neighboring points (cross-sections) along the line. The effect of continuous change of current (flux) and electric (magnetic) difference of potentials along the line takes place because lines have distributed longitudinal and lateral elements.

In electrical lines with distributed parameters, the longitudinal elements are formed by the active resistances of the wires of the line and by the inductances of the two opposite line sections with length dx. Lateral elements consist of leakage resistances, formed as a result of imperfections in the insulation between the wires of the line and capacitances formed by the opposite sections (elements) of the line.

In magnetic lines with distributed parameters, the longitudinal elements are the magnetic resistances of magnetic rods that form magnetic lines. Lateral resistances are caused by the leakage of magnetic flux through the air between opposite sections of the line.

A line with non-distributed parameters is called a homogeneous line, when all longitudinal resistances of the sections of the line with the same length are equal, and all lateral resistances of the sections of the line with the same length are equal. A line with distributed parameters is called a non-homogeneous line, when longitudinal and lateral resistances in the line are different. Two groups of lines with distributed parameters are referred to as linear and non-linear lines. In non-linear lines with distributed parameters the longitudinal and/or lateral resistances are functions of the currents passing through the line. In the linear lines both longitudinal and lateral resistances are not functions of the currents passing through the line.

An example of a non-linear electrical line with distributed parameters is a high-voltage electric power line during a silent electrical discharge (corona discharge on wires) between the wires of the line. In this case, the capacitance between opposite sections of the line will be functions of the voltage between these sections The phrase "line with distributed parameters" is normally applied to the lines for transmission of electrical energy over long distances, telephone and telegraph aerial and cable lines, railway lines of automatic block-systems, antennas in radio technology and other related lines and installations. Even when there are no actual "lines", it is still possible to have lines with distributed parameters. For example, a normal inductance coil at frequencies high enough is a line with distributed parameters formed by inductance, inter-turn capacitances and capacitances to the case of device. When there is an alternating current in the coil, there is a current in the capacitances as well. At the same voltage between neighboring turns, the current through the capacitances rises with increasing alternating current frequency. At low frequencies (up to several thousand Hertz) little error is generally introduced by failing to take into account the current passing through capacitances.

At high frequencies, such as hundreds GHz, the currents passing through the capacitances can be much higher than the currents in the coil. In this case, the coil as whole has to be considered in terms of capacitive impedance, rather than inductive impedance. At the intermediate frequencies of the order of several MHz, when the linear size of the coil is comparable with the wavelength, the inductance coil is a typical example of a line having distributed parameters.

When an inductance coil is reeled up around a steel core to form a coil device, the coil device having the ability to saturate, and the frequency of the current is high enough, the coil device becomes a complex composition of electrical and magnetic non-linear circuits with distributed parameters. The classical example of an electric and magnetic non-linear line with distributed parameters is the three-phase system of electric power transmission. A three phase systems of electric power transmission consist of energy sources, transmission lines, transformers, electric engines and other electric machines. As a result of any fault, such as a short circuit or break of wire or under an asymmetric load on the elements of the system, such as a transmission line, current and voltage oscillations can occur. These oscillations can include:

1. Oscillations on the highest harmonic;
2. Sub-harmonic oscillations with the frequency equal to $\psi/n$;
3. Oscillations with a frequency equal to $m\psi/n$, where m and n are integer numbers;
4. Self-modulations; and.
5. Chaotic oscillations and alternating resonances.

In power, telephone, and telegraph and similar devices containing lines with distributed parameters current and voltage oscillations can occur during the connection of the line to the signal source, during disconnection from the signal source, during connection or disconnection of a load, or in the case of atmospherics (e.g. lightening) /11/. Therefore any electric or magnetic circuit with distributed parameters can be considered to be capable of being a multimode self-sustained oscillation system having a finite probability of operation in the concurrence of modes condition.

An important identifying feature characteristic of operation in the concurrence of modes condition is its pulse character. Pulse character is used herein to refer to the process whereby pulses of energy are transfer between modes, which simultaneously exist during operation in the concurrence of modes condition. Pulse character is characterized by a jump (step) in the amplitude certain parameters, such as voltage or current. Therefore, an oscillogram representation of this process will appear as an oscillation amplitude surge (or reduction) in the amplitude of current or voltage resulting pulse-like portion (see curve 3 on FIG. 8 near r=5).

Concurrence of modes in a rectangular cavity resonator is now considered. In a rectangular resonators /12/, coexistence of the modes $TE_{mnp}$ and modes $TM_{mnp}$ is possible under certain conditions. Indices m, n and p are numbers of standing semi-waves in the directions x, y and z, respectively. Modes are formed from the waves of type $TE_{mn}$ and $TM_{mn}$ in the waveguide due to the selection of the resonator length equal to $(p/2)\lambda_g$, where $\lambda_g$ is the wavelength of the electromagnetic wave inside the waveguide. In a rectangular copper waveguide operating at a frequency of approximately 10 GHz, the principal mode is $TE_{10}$, then mode $TE_{20}$, $TM_{11}$ and $TE_{11}$. The principal and other oscillation modes are defined by the geometry of the waveguide.

Under typical operation or in the absence of concurrence of modes condition, waves $TE_{mn}$ and $TM_{mn}$ have exponential damping. Their rise could be described by the function $1-e^{-\alpha r}$, and their damping by the function $e^{\alpha(r_0-r)}$ (see curve 1, FIG. 8).

Under low power, a super high frequency (SHF) power supply coupled into the resonator results in weak dispersion, wherein redistribution of mode energy between several oscillation modes can begin. As a result, fast-damping oscillations can emerge in the system with damping dependence as $$\sim \frac{1}{r^2}$$

(curve 2, FIG. 8), or slow damping oscillations with damping dependence like $$\sim \frac{1}{\sqrt{r}}$$

Figure 8:
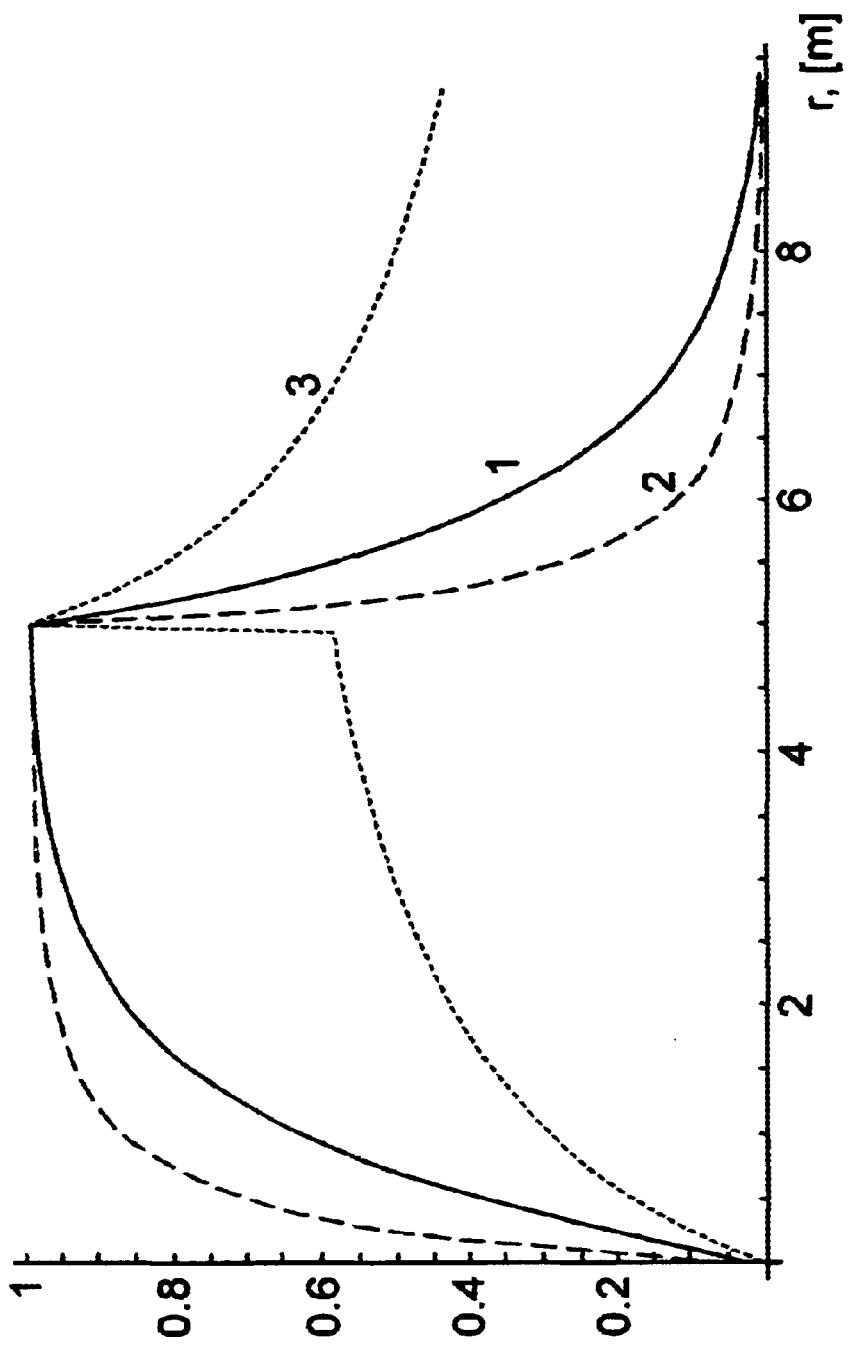
FIG. 8 illustrates the form of various pulses operable during a representative concurrence of modes condition.

(curve 3, FIG. 8).

Transitions from the regime of generation of one mode to the regime of generation of another mode generally occurs by an abrupt change and characterized by an amplitude function such as, voltage or current, evidencing a tailing effect (curve 3, FIG. 8; abrupt change near r=5).

Modes $TE_{mn}$ and $TM_{mn}$ induce electric charges to reside on the walls of waveguide and rectangular resonator. The electric charges induced have a well-defined spatial structure, thus defining the spatial direction of $\vec{\nabla}\phi$. In approximation of the principal mode $TE_{102}$, the processes of spatial distribution of electric charges and conductivity current can be defined as follows [12]. The lines of electric field are defined by a single component as shown below:

$$E_y = i\sqrt{\frac{\mu}{\varepsilon}}\sin\left[\frac{\pi x}{a}\right]\sin\left[\frac{2\pi z}{d}\right] \qquad 42$$

Where $\alpha$ and d are dimensions of the resonator in directions x and z respectively. The magnetic field components are as follows:

$$H_x = \frac{H_0}{\sqrt{1+(d/2a)^2}}\sin\left[\frac{\pi x}{a}\right]\cos\left[\frac{2\pi z}{d}\right] \qquad 43$$

$$H_z = \frac{-H_0}{\sqrt{1+(2a/d)^2}}\cos\left[\frac{\pi x}{a}\right]\sin\left[\frac{2\pi z}{d}\right]$$

In the above expression $TE_{xyz}$ the first number of the index shows the number of standing half-waves in the direction x, x being the height of resonator (or wave-guide). The second number of the index means number of standing half-waves in the direction y, the direction y being the width of the resonator (or waveguide). The third number z is the number of standing half-waves in the direction z, the direction z being the length of resonator (or wave-guide). Since the length of the waveguide (z) may be very large, in order to characterize the oscillations in the wave-guide it is conventional to only use first two numbers of the index. For example, a $TE_{10}$ mode of a given resonator will corresponds to the $TE_{102}$ mode of the waveguide, the z=2 mode being the primary mode for a particular waveguide.

Figure 9:
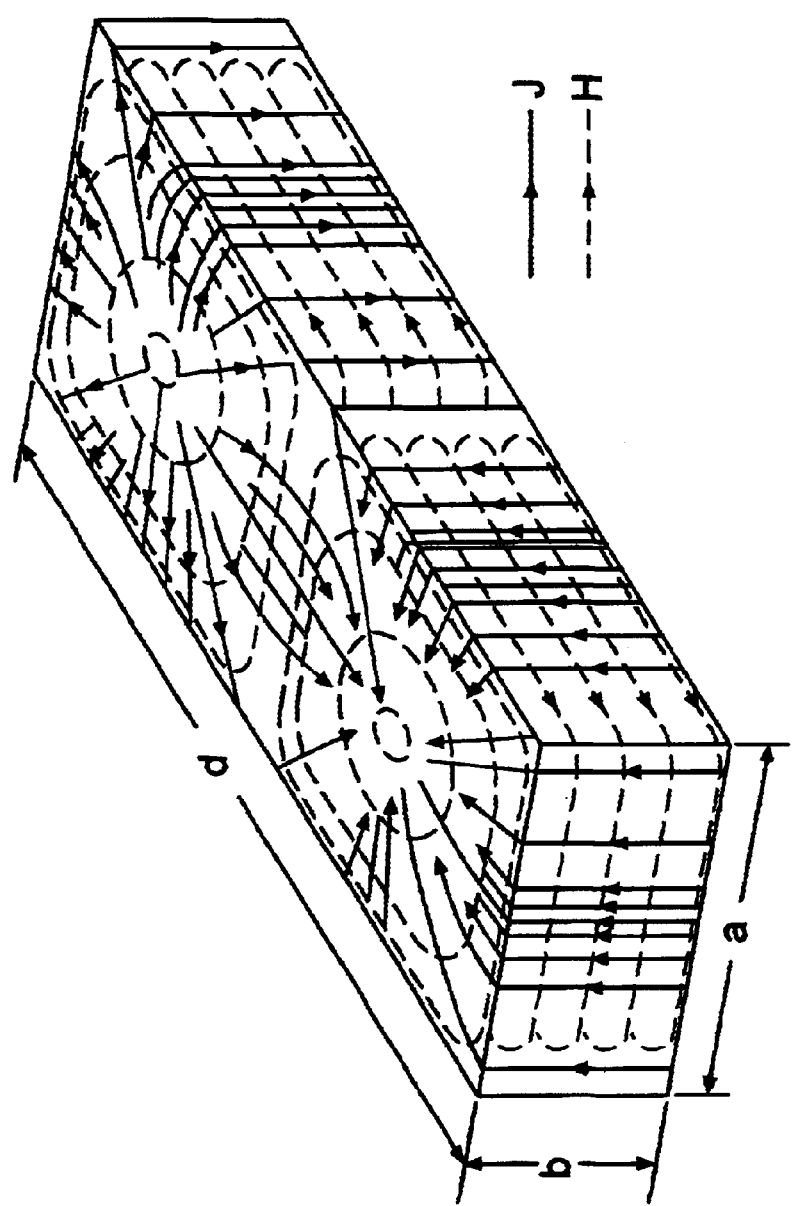
FIG. 9 illustrates a distribution of the electrical current density vector ($\vec{J}$) and magnetic induction vector ($\vec{H}$) in a rectangular resonator.

FIG. 9 illustrates a distribution of the electrical current density vector (>J) and magnetic induction vector (>H) in a rectangular resonator. Electric field lines (42) can be seen to start and finish on the charges induced on the wide wall (plane xz) of the resonator. The magnetic field (43), which is parallel to the walls of the resonator, induces the walls currents of conductivity in a direction perpendicular direction to the magnetic field. Electric current is controlled by the displacement current (D) that flows through the centers of the loops of magnetic lines and induces electric charges on the wide wall (plane xz) near the said centers. The induced currents change sign after each half-period. In order to form induced charges, electrons are passed back and forward through the resonator's wall during each half-period. As a result Ohmic losses are believed to occur.

Changes in the resonator quality (Q) become negligible upon reduction of the supplied SHF power to low power. Therefore, the process of transition into operation in the concurrence of mode condition may be considered by approximating the resonator quality (Q) to be a constant.

Concurrence between modes at weak coupling leads to the abrupt changes of mode energy due to nonlinear redistribution of energy between respective modes. This energy exchange process causes changes in speed of damping of oscillations $TE_{mn}$ and $TM_{mn}$. Therefore, there is a connection between induced electric charges and oscillation modes in the resonator.

The spatial structure of induced currents unambiguously defines $\vec{\nabla}\phi$. According to (31), (37) and (39), the definition of the spatial direction of $\vec{\nabla}\phi$ leads to the definition of the directional derivatives (36). As a result, the D'Alembert solution (14) for the wave of vector potential $\vec{A}$ becomes valid.

In accordance with (38), changes of $\vec{\nabla}\phi$ and $\vec{j}_c$ are connected to one another. Accordingly, changes in $\vec{\nabla}\phi$ during the operation in the concurrence of modes condition in a self-sustained oscillation system, such as a resonator, can result in emergence of oscillations of conductivity current density. These oscillations will damp faster or slower than exponential oscillations of type $e^{-\alpha r}e^{-ikr}$. In accordance to (36), oscillations of the conductivity current density $\vec{j}_c$ define contributions into the wave of vector potential $\vec{A}$. It is the third member (double integrals) in the right-hand part of (14) and (32). It is labeled by the symbol $\vec{A}_2$, and it has the following form:

$$\vec{A}_2 = \frac{\mu_0}{4} \int_{r-at}^{r+at} dr \int_{r-at}^{r+at} \mu \vec{j}_c dr \qquad 44$$

In accordance with the graphs of test-functions (see FIGS. 1–7 and comments), the wave component of vector potential $\vec{A}$ (44) that satisfies to the condition (41) will cause excitation of chemical bonds electrons by action of an electromagnetic field, provided that the damping oscillations is faster or slower than exponential damping described by function of type $e^{-\alpha r}$, where $\alpha$ is the real attenuation constant, r is the direction of oscillation propagation. In both cases in the range of $r \leq 2\alpha$ function $\vec{A}_2$ is linear and decreases as:

$$\vec{A}_2 \sim A * 2at\left(1 - \frac{\vec{r}}{2at}\right) \qquad 45$$

In view of the above, a number of conclusions can be drawn. In order to excite chemical bond electrons by action of an electromagnetic field, it is necessary to use a multi-mode self-sustained oscillation system having well-defined spatial direction of $$\vec{\nabla}\varphi, \quad \text{or} \quad \frac{\partial}{\partial r}\vec{\nabla}\varphi, \quad \text{or} \quad \frac{\partial^2}{\partial r^2}\vec{\nabla}\varphi,$$

or well-defined spatial structure of both $\epsilon$ and $\mu$, given that the system operates in the concurrence of modes condition.

Under operation in the concurrence of modes condition, the oscillations of conductivity current density $\vec{j}_c$ emerge with a different damping function from the exponential one of type $e^{-\alpha r}$. These oscillations of conductivity current density form the component of the wave of vector potential $\vec{A}$ that satisfies (45), decreasing linearly with distance. Interaction between the electromagnetic field with such a form of vector potential (integral characteristic in relation to $\vec{E}$ and $\vec{H}$) and matter will result in the excitation of chemical bonds of the matter.

Operation in the concurrence of modes condition can produce a single pulse if coupling between modes is strong enough or a series of pulses (quasi-pulse regime) in the case of weak coupling. Thus, the method of excitation of chemical bonds consists of excitation of chemical bonds in molecules of matter under the effect of electromagnetic field formed by a multi-mode self-sustained oscillating system operating in the concurrence of modes condition.

The excitation of a chemical bond is a quantum effect. Accordingly, to generate the excitation, special equipment is preferably provided. To generate and observe excitation of chemical bonds, electron spin resonance spectrometers (ESR spectrometers) can be used. ESR spectrometers consist of a SHF-generator loaded on a cavity resonator placed into a constant magnetic field. Changes in the cavity resonator are registered by a very precise system of registration. The signals registered can be correlated with changes of magnetic moment of electrons.

ESR-spectrometers are preferred systems for the study and registration of changes in electron states and accordingly, an ideal instrument for demonstration of the invention. An ESR spectrometer provides both spatial and time synchronism automatically because the geometry of waveguide and resonator simultaneously define several connected TE and TM oscillation modes. During operation, one principal mode is used. Other modes are also present but have much less energy. At high power, the selected mode will suppress other modes and will prevent the system from operating in the concurrence of modes condition. An appropriate reduction in power directed to the resonator can result in a decrease of the energy of the principal mode and increase of energy of other modes. As a result, the energy of the non-principal modes can become comparable to the principal mode and the concurrence of modes condition occurs. Accordingly, in the examples to follow, the SHF-power is reduced to a minimum value provided by the system to obtain operation of the spectrometer in the concurrence of modes condition.

It should be understood that the examples and embodiments described herein are for illustrative purposes only and that various modifications or changes in lightthereof will be suggested to persons skilled in the art and are to be included within the spirit and purview of this application. The invention can take other specific forms without departing from the spirit or essential attributes thereof.

EXAMPLE 1

A Spectrometer model ERS-220 having a rectangular resonator was used, with the working frequency of f~10

GHz. The internal dimensions of the resonator were, the length equal to 4.5 cm, height equal to 2.25 cm and width equal to 1 cm. In this system, mode $TE_{10}$ is principal, followed by mode $TE_{20}$, mode $TM_{11}$ and mode $TE_{11}$. Under normal conditions when there is no concurrence of modes operation, the modes $TE_{mn}$ and $TM_{mn}$ each have an exponential character of attenuation.

In order to tune the spectrometer into operation in the concurrence of modes condition, the power supplied to the resonator was reduced to the limit value at which generation exists but is very close to breakdown. The value of power used was equal to approximately 50 mW. At this power level in the resonator, redistribution of energy among oscillation modes occurs, resulting in operation of the resonator system in the concurrence of modes condition. The operation of the system in the concurrence of mode condition can be observed on the spectrometer's oscilloscope in the form of a weak tremor of the absorption curve of the generation zone. Thus, the presence of the concurrence of mode condition can be observed by noting a weak tremor on the arrow indicator of the PLL (Phase Locked Loop) block of SHF stabilization, and of the arrows on diode current indicators.

Such a tremor is the result of the setting up of weak coupling between the various waveguide modes, which cause the appearance of quasi-periodic pulses due to abrupt exchange of energy between concurrent modes. Pulse repetition frequency is on the order of tens of Hertz.

Therefore, to operate in the concurrence of modes condition, one needs to use a low-frequency registration block with the modulation frequency $f_{mod} \leq 20$ Hz to observe the concurrence of mode condition. The modulation frequency $f_{mod}$ must be minimal in order to satisfy the following inequality:

$$f_{mod} << \frac{1}{T_{mn}}$$

Where $T_{mn}$ is the average pulse repetition time of quasi-pulses in the concurrence of modes condition.

If the modulation frequency becomes comparable or higher than the inverse value of time $T_{mn}$, the change of magnetic field occurs too fast and the spin system does not have time to follow these changes. Such a situation leads to the reduction of the amplitude of the pulse-like signal under detection and can result in the complete disappearance of the signal. Therefore the usage of a high-frequency registration block is not efficient for the registration of resonance absorption curve and in the best case will allow the observation of only a small drift of a zero-line.

Spectral pure optical quartz (Bruker) was used as a test-object. The quartz was a section of a quartz ampoule with a diameter of 5 mm, having a wall thickness equal to 0.5 mm and height equal to 2.25 cm. The choice of spectral pure optical quartz was made based on the following considerations:

1. In spectral pure optical quartz, the content of impurities corresponds to the spectral standards and there are practically no active centers with unpaired electrons. Therefore ESR-signals detected can only appear due to excitation of electrons of chemical bonds between atoms of silicon and oxygen.
2. There is no long-range order in the amorphous quartz glass. That is why excitation of the chemical bonds occurs as a result of direct interaction between the electromagnetic field with a vector potential component satisfying condition (45) and the first coordination sphere of silicon.
3. Quartz glass has strong chemical bonds and demonstration of their excitation is a good example of the action of the electromagnetic field with vector potential ($\vec{A}$) wave component satisfying (45).

Quartz glass was placed into the rectangular resonator under room temperature conditions. In order to be able to make comparisons, the spectrum of ESR is recorded in regular regime, a nominal power value of 250 mW. Under these conditions, it was verified that there is no spin response from the sample under investigation (FIG. 10, spectrum 1) in the regular regime. The ESR-spectrometer was then tuned into the concurrence of modes conditions (see above). The signal of electron spin resonance was then detected (FIG. 10, spectrum 2). Local areas of instability of the electron wave function, probably sp hybrid orbitals of silicon atoms, are likely responsible for the electron spin signals detected.

In case of probabilistic distribution of these areas (surface defects, for example), due to the lack of long-range order in the quartz glass, the intensity of spin response would be expected to remain constant and not depend on time of exposition of the sample to the applied electromagnetic field. However the spin response and its intensity was seen to depend on the time of exposition. Therefore, it was concluded that structural quartz anomalies, such as defects, could not be responsible for the detected ESR signal.

The analysis of ESR spectrums obtained allows definition of the mechanism of consecutive, avalanche-like excitation of chemical bonds. Its essence is believed to be explained by the following theory. The component of vector potential ($\vec{A}$) satisfying (45) is formed in a quasi-pulse regime, and at the initial stage an electromagnetic field excites chemical bonds that have local instability of the electron wave function. Such selectivity is defined by the reduced relaxation time of the chemical bonds with one or more types of local instability. Further time of exposing the quartz glass after the initial stage to an electromagnetic field with vector potential wave component satisfying (45) leads to avalanche-like excitation of chemical bond electrons, which bind the atoms of silicon and oxygen. From the beginning of the process, the weakest non-bonding electron states (orbitals) are excited. Subsequently, these excited non-binding electron states permit initiation of excitation of stronger bonding electron states (orbitals). The process of avalanche-like excitation of chemical bonds is registered by the ESR-spectrometer in the form of rising intensity of spin response with increasing time of exposition to electromagnetic fields having a vector potential $\vec{A}$ component satisfying equation (45).

EXAMPLE 2

A modulation spectrometer model ESP-300e (BRUKER) was used, equipped with a temperature attachment and a device to rotate samples inside the rectangular resonator model 9304st371 Conditions for fine-tuning and operating the spectrometer in the concurrence of modes condition were analogous to those described above relative to EXAMPLE 1. In this example, the pumping of chemical bonds by electromagnetic radiation was investigated.

General requirements for a suitable object for electromagnetic pumping of chemical bonds can be formulated as follows. The object must have a rarefied spectrum of the proper oscillations to provide maximum inter-mode distance. In order to estimate the degree of rarefaction of the spectrum of the object for proper oscillations, experimental data on the conductivity anisotropy, thermo-EMF, and/or the data on the superfine interactions in the axial symmetry approximation may be used. The larger the anisotropy of the above parameters, the better a sample is suited for electromagnetic chemical bond pumping.

Monocrystals of the oxygen vanadium bronzes $Na_xV_2O_5$ of β-type, where x=0.22; 0.27; 0.33 were used. The crystalline structure of β–$Na_xV_2O_5$ belongs to the monoclinic syngony, spatial group C2/m. The electrical conductivity at 300 K along axis b is on the order of 100 $\Omega^{-1}$ $cm^{-1}$, that being approximately two orders of magnitude more than the conductivity in the direction perpendicular to axis b. The data on the conductivity anisotropy and thermo-EMF are presented in [13].

The electron structure of β–$Na_xV_2O_5$ is as follows. Sodium atoms have an electron configuration of $3s^0$. The electron configuration for Na metal is $3s^1$. However, the vanadium bronze configuration of Na is $3s^0$ since it is in an ionized state. The $3s^1$ electron from metal Na is transferred to vanadium ions, reducing the vanadium ions' valence from +5 to +4. Oxygen atoms have an outer shell electron state $2p^6$. Vanadium atoms are in the electron states with the configurations $3d^1$ and $3d^2$—singlet, the number of states $3d^1$ approximately being equal to x. In the axial symmetry approximation, the vanadium $3d^2$—singlet states occupy two structurally non-equivalent positions V(1) and V(2) that are clearly revealed in the difference of the parameters of the quadrupole interaction β–$Na_xV_2O_5$ [14] (FIG. 13).

Two phase transitions under temperatures $T_1$~160 K and $T_2$~110 K are observed in compound $Na_xV_2O_5$. In addition, under temperatures below 200 K, the displacement of vanadium atoms along crystal axis b [15] and the change of the anisotropy parameters of the thermo-EMF in the same temperature interval [13] were found. Taking into consideration the connection of the anisotropy parameters with the rarefaction of the spectrum of the proper oscillations, it was concluded that the variation of the temperature of the sample within the range of 100 to 200 K could be used for the selection of the mode composition in β–$Na_2V_2O_5$.

Creation of inverted differences in population of the two (2) energy levels of $3d^2$—states of vanadium atoms were believed possible using appropriate electromagnetic excitation, these electrons occupying the $3d^2$—states forming chemical bonds with the atoms of oxygen. As in a laser, an inverse difference in population of energy levels, where the higher energy state is more populated than a corresponding lower energy state, can lead to stimulated electromagnetic radiation from the lasing material.

The stimulated electromagnetic radiation emitted by the crystal can be registered by the ESR-spectrometer in the form of modulation signals that are opposite in phase as compared to the regular ESR-signals emitted by the crystal. Due to the fact that the phase tuning of the spectrometer is fixed and cannot be changed, and sensitivity of the system of registration is very high, the emergence of stimulated electromagnetic radiation registered by the ESR-spectrometer is an unambiguous indication of the emergence of stimulated electromagnetic radiation.

Monocrystalline β–$Na_xV_2O_5$ was placed into the rectangular resonator provided by the Bruker spectrometer. The ESR-spectrometer was tuned into the concurrence of modes operation, (see EXAMPLE 1 for conditions). Using the low-frequency registration block, an extremely intense and wide absorption line was observed from excited chemical bonds formed between $3d^2$ states of vanadium atom electrons and atoms of oxygen. Estimation of the active centers concentration gives the number of order ~$10^{23}$. Since the creation of the inverse population of the chemical bonds energy levels was investigated in this example, signals from $3d^2$ states of vanadium were not considered. Accordingly, the high-frequency block of registration was used. The ESR-signal from the unpaired electrons of vanadium in the configuration $3d^1$ was investigated using a standard modulation signal.

Figure 11:
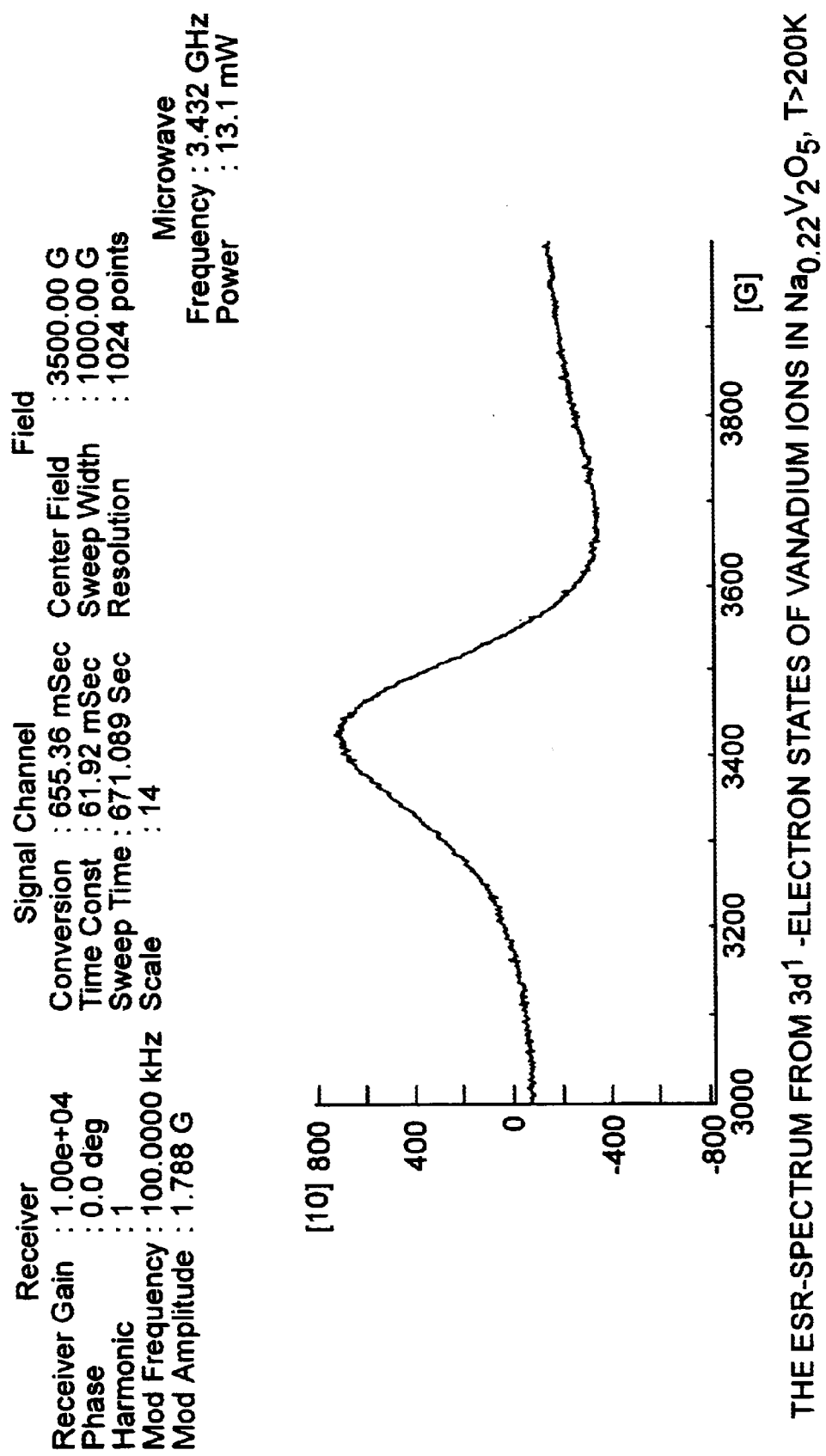
FIG. 11 illustrates the ESR spectrum from vanadium ions in $Na_{0.22}V_2O_5$ at a temperature of 200 K.
Figure 12:
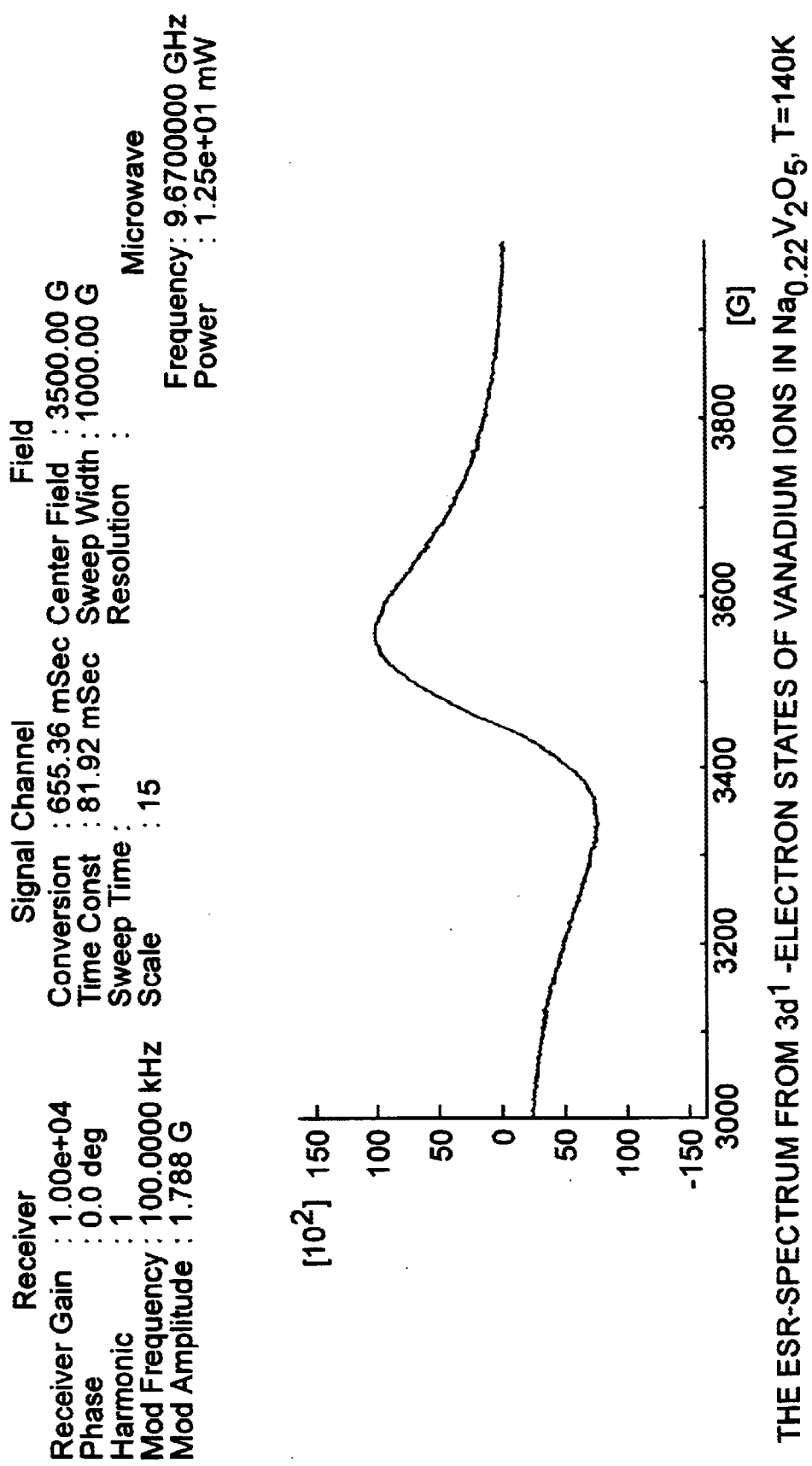
FIG. 12 illustrates the ESR spectrum from vanadium ions in $Na_{0.22}V_2O_5$ at a temperature of 140 K.

At temperatures above approximately 200 K, the ESR-spectrometer registered a single line from $3d^1$ states (FIG. 11). Below this temperature, approximately from 150 K or below, low-frequency beats emerge that can be observed on the spectrometer oscilloscope. Then a stable generation of electromagnetic radiation from the crystal begins, and a signal from the $3d^1$ V electrons begins to be registered in the opposite phase evidencing stimulated electromagnetic radiation emitted by the crystal (FIG. 12).

The stimulated electromagnetic radiation activity level of crystals of β–$Na_xV_2O_5$ was found to depend upon the concentration (x) of sodium ions. Thus, the highest activity is demonstrated by the monocrystals of $Na_{0.22}V_2O_5$ composition, the excitation of chemical bonds of which takes place in a wide range of temperatures. Monocrystals of $Na_{0.33}V_2O_5$ posses a narrower temperature range of excitation, and are very sensitive to crystal orientation. There was no success in obtaining the excitation of chemical bonds under the above conditions for $Na_{0.27}V_2O_5$ monocrystals.

Conclusions based on the above Examples

It follows from Example 1 that the invention can be used for characterization of materials. Most inorganic materials and the overwhelming majority of organic materials do not have unpaired electrons. These materials cannot be characterized by conventional methods of ESR-spectrometry. The method of chemical bond excitation described in this invention makes it possible to characterize inorganic or organic materials, which lack unpaired electrons. The information obtained by ESR-spectrometry provides direct information regarding electron states of atoms that form chemical bonds. Such data can be useful for a variety of applications, such as in the chemical, metallurgical, pharmaceutical and food industries. It can allow quality control of production with high precision. The invention may also be used to control chemical reactions by controlling the formation of chemical bonds in chemical reactions to permit (or aid in) the synthesis of a variety of compounds.

Based on the results shown Example 1, this invention could also be used for the scanning of complex organic compounds or biological organisms, such as bacteria. The combination of single pulses and pulse repetitions of electromagnetic waves with vector potential components satisfying (45) allows for excitation of selected chemical bonds. Thus, the invention provides the possibility of carrying out ESR-spectrometry of complex organic materials or even biological organisms.

Based on results demonstrated in Example 2, the invention could be used in the field of quantum generators and amplifiers. Taking into consideration the number of paramagnetic centers in active media represented by chemical bonds, the invention may have utility to increase the power output of MASERS, LASERS and related quantum amplification devices.

Quantum amplification on chemical bonds is capable of producing outputs having very low level of noise. Normally the fluctuations of electron density on active centers are responsible for noise. In this regard, it is exactly the electrons of chemical bonds that have minimal fluctuations of electron density and therefore produce minimal levels of proper noise for any active media.

It follows also from Example 2 that the invention may find use for measurements of the vector potential of electromagnetic fields. For this purpose, quantum amplifiers based on excitation of chemical bonds could be used.

There are many additional applications for this invention, such as synthesis of complex organic compounds. There is a problem of selective excitation of certain chemical bonds in organic macromolecules. The use of theinvention to resolve problems of synthesis of organic compounds may allow the efficiencies, which can reduce production costs. Production of new and/or improved monocrystals may also be possible using the invention. Selective excitation of chemical bonds in the process of crystal growing allows magnetic and dielectric parameters of materials to be changed. For example, it may be possible to change certain diamagnetic crystal to strong paramagnetic ones. This type of technology applications could lead to changes in various fields, such as microelectronics and opto-electronics.

REFERENCES

1. E. L. Feinberg, Propagation of radio-waves along the earth surface.-Second ed.-Moscow, Nauka, Fizmatgiz, 1999.-496p. ISBN 5-02-015243-9.
2. L. A. Vainstein, Electromagnetic waves.-Second ed., Moscow, Radio i Svyaz, 1988.-440p. ISBN 5-256-00064-0.
3. H. Eyring, J. Walter and E. Kimball, Quantum chemistry.-Moscow, Inostrannaya literature, 1948.-527p.
4. C. Zener, Phys., Rev. 36, 51 (1930).
5. J. C. Slater, Phys., Rev., 36, 57, (1930).
6. N. Rozen, Phys., Rev., 38, 2099, (1931)
7. Physical Encyclopedic Dictionary, Chief Ed. A. M. Prokhorov.-Moscow, Soviet Encyclopedia, 1983.-928p.
8. Mathematical Handbook for scientists and engineers. Definitions, Theorems and formulas for reference and review. G. A. Korn, T. M. Korn, McGraw-Hill Book Company, New York, San Francisco, Toronto, London, Sydney, 1968.
9. A. Erdely et al., Higher transcendental functions, vol. 1, 2. McGraw-Hill Book Company, New York, N.Y., 1953.
10. L. K. Martinson, Yu. I. Malov, Differential equations of mathematical physics.-Moscow, MGTU im. Bauman, 1996 (Series Mathematics in the technological university, ed. XII).
11. L. A. Bessonov, Theoretical basics of electrical engineering. Electrical circuits. Textbook,-10-th ed., Moscow, Gardariki, 2000, 638p.
12. C. P. Pool, Jr., Electron spin resonance. Comprehensive treatise on experimental techniques, Interscience Publishers. $\vec{A}$ division of John Wiley & Sons, New York, London, Sydney, 1967.
13. P. Y. Novak, A. A. Fotiev, Doklady Akademii Nauk (Reports of the Academy Of Science of the USSR), v.289, no.5, p.1164, 1986.
14. N. A. Zhuravlev et al., Journal of structural chemistry, v.31, no.10, p.56, 1989.
15. Y. Kanai, S. Kagishima, H. Nagasava, Syntetic Metals, no.9, p.59, 1990.

APPENDIX

Proof of the theorem $\vec{\nabla} \times (\vec{\nabla} \times \vec{A}) = -\vec{A}"$.
The basis unit vectors of the Cartesian system of coordinates are denoted by the symbols $\hat{b},\hat{t},\hat{n}$. The choice of such a notation is defined as follows. Generally, the arbitrary orthogonal system of coordinates can always be obtained in the form of a moving trihedral, with the ribs formed by unit vectors of $\hat{b}$ - bi-normal, $\hat{t}$ - tangent line and $\hat{n}$ - principal normal for the given spatial curve [8]. Correspondently, any arbitrary vector $\vec{a}$ can be represented in the form of:
$\vec{a} = \{x_0, y_0, z_0\} = x_0\hat{b} + y_0\hat{t} + z_0\hat{n}$
It can be assumed that trihedral $\hat{b},\hat{t},\hat{n}$ corresponds to the right-hand system of coordinates:
$\hat{n} = \hat{b} \times \hat{t}$  $\hat{t} = \hat{n} \times \hat{b}$  $\hat{b} = \hat{t} \times \hat{n}$
The straightening plane $\hat{b},\hat{t}$ can be aligned with the plane Re[f],Im[f]:
$\hat{b} = \vec{e}_{Re[f]}$  $\hat{t} = \vec{e}_{Im[f]}$
Where $\vec{e}_{Re[f]}$ and $\vec{e}_{Im[f]}$ - unit-vectors of real and imaginary parts of the complex function.
It is assumed that complex function depends on the single argument r with the axis directed along unit-vector of a principal normal $\hat{n}$:
$\hat{n} = \vec{e}_r$
The real and imaginary parts of the complex function can be labeled with the symbols k and $\tau$:
$k = \rho\cos\phi = Re[f]$  $\tau = \rho\sin\phi = Im[f]$
Generally, we have to consider two inter-orthogonal functions on the complex plane, which we will label with the symbols f(r) and h(r):
$\vec{f} = \rho(\cos\phi\hat{b} + \sin\phi\hat{t}) = k\hat{b} + \tau\hat{t}$
$\vec{h} = \rho(-\sin\phi\hat{b} + \cos\phi\hat{t}) = -\tau\hat{b} + k\hat{t}$
Connection between $\hat{f}$ and $\hat{h}$:
$\hat{h} = \hat{n} \times \hat{f}$
Or in the scalar form:
$h(r) = if(r)$
Multiplication on imaginary unit in the scalar form corresponds to the vector multiplication (from the right side) of the vector of the principal normal on the vector of the complex function.
Derivatives of the functions f' and h' in scalar form are:
$f' = (\rho e^{i\phi})' = (\rho' + i\rho\phi')e^{i\phi}$
$h' = (i\rho e^{i\phi})' = (i\rho' - \rho\phi')e^{i\phi}$
The corresponding vector form is:

$$\vec{f}' = \frac{\rho'}{\rho}\vec{f} + \varphi'(\vec{n} \times \vec{f}) = \frac{\rho'}{\rho}\vec{f} + \varphi'\vec{h} \qquad 20$$

$$\vec{h}' = \frac{\rho'}{\rho}(\vec{n} \times \vec{f}) - \varphi'\vec{f} = \frac{\rho'}{\rho}\vec{h} - \varphi'\vec{f}$$

$\vec{\nabla} \times \vec{f}$ is considered:
$\vec{\nabla} \times \vec{f} = \vec{\nabla}k \times \hat{b} + \vec{\nabla}\tau \times \hat{t}$  (21)
The right part of the expression (21) is transformed:
$\vec{\nabla}k \times \hat{b} = -\hat{b} \times \vec{\nabla}k = \hat{n} \times \hat{t} \times \vec{\nabla}k = \hat{t}(\hat{n}, \vec{\nabla}k)$  (22)
$\vec{\nabla}\tau \times \hat{t} = -\hat{t} \times \vec{\nabla}\tau = -\hat{n} \times \hat{b} \times \vec{\nabla}\tau = -\hat{b}(\hat{n}, \vec{\nabla}\tau)$
In the expression (22) the rule of transformation for the double vector multiplication was used:
$\vec{a} \times (\vec{b} \times \vec{c}) = \vec{b}(\vec{a}, \vec{c}) - \vec{c}(\vec{a}, \vec{b})$
In the spherical system of coordinates the gradient of scalar function $\vec{\nabla}k$ has the form of:

$$\vec{\nabla}k = \frac{\partial k}{\partial r}\vec{e}_r + \frac{1}{r}\frac{\partial k}{\partial \theta}\vec{e}_\theta + \frac{1}{r\sin\theta}\frac{\partial k}{\partial \phi}\vec{e}_\phi$$

Directional derivative of the radius-vector k' is equal to:

$$k' \equiv \frac{\partial k}{\partial r} = (\vec{e}_r, \vec{\nabla}k)$$

Where $\vec{e}_r, \vec{e}_\theta, \vec{e}_\phi$ - vector-units of the spherical coordinates r,θ,φ.
In this case $\vec{e}_r = \hat{n}$, therefore from the expressions (22) we have:
$\vec{\nabla}k \times \hat{b} = \hat{t}(\hat{n}, \vec{\nabla}k) = k'\hat{t}$  $\vec{\nabla}\tau \times \hat{t} = -\hat{b}(\hat{n}, \vec{\nabla}\tau) = -\tau'\hat{b}$  (23)
By the substitution of (23) into (21) we find:
$\vec{\nabla} \times \hat{f} = k'\hat{t} - \tau'\hat{b}$  (24a)
By analogy for $\hat{h}$ we have:
$\vec{\nabla} \times \hat{h} = -\tau'\hat{t} - k'\hat{b}$  (24b)
Expressions for derivatives k' и τ' can be written as follows:
$k' \equiv (\rho\cos\phi)' = \rho'\cos\phi - \phi'\rho\sin\phi$
$\tau' \equiv (\rho\sin\phi)' = \rho'\sin\phi + \phi'\rho\cos\phi$
Hence:

APPENDIX-continued $$\vec{\nabla} \times \vec{f} = \rho'(-\sin\varphi \vec{b} + \cos\varphi \vec{t}) - \varphi'\rho(\cos\varphi \vec{b} + \sin\varphi \vec{t}) = \frac{\rho'}{\rho}\vec{h} - \varphi'\vec{f} \quad (25)$$

$$\vec{\nabla} \times \vec{h} = -\rho'(\cos\varphi \vec{b} + \sin\varphi \vec{t}) - \varphi'\rho(\cos\varphi \vec{t} - \sin\varphi \vec{b}) = -\frac{\rho'}{\rho}\vec{f} - \varphi'\vec{h}$$

Comparison of (25) with (20) gives:
$\vec{\nabla} \times \vec{f} = \vec{h}'$ $\qquad \vec{\nabla} \times \vec{h} = -\vec{f}'$ (26)
From (24) the recurrent operation can be found:
$\vec{\nabla} \times (\vec{\nabla} \times \vec{f}) = -k''\vec{b} - \tau''\vec{t} = -\vec{f}''$
$\vec{\nabla} \times (\vec{\nabla} \times \vec{h}) = \tau''\vec{b} - k''\vec{t} = -\vec{h}''$ (27)
The connection between directional derivative and time derivative is:

$$\vec{f}' = \frac{1}{a}\frac{\partial \vec{f}}{\partial t}$$

Where a - phase speed.
Correspondingly:

$$\vec{\nabla} \times \vec{f} = \frac{1}{a}\frac{\partial \vec{h}}{\partial t} \qquad \vec{\nabla} \times \vec{h} = -\frac{1}{a}\frac{\partial \vec{f}}{\partial t} \quad (28)$$

$$\vec{\nabla} \times (\vec{\nabla} \times \vec{f}) = -\frac{1}{a^2}\frac{\partial^2 \vec{f}}{\partial t^2} \qquad \vec{\nabla} \times (\vec{\nabla} \times \vec{h}) = -\frac{1}{a^2}\frac{\partial^2 \vec{h}}{\partial t^2}$$

The proof of the theorem is finished.

What is claimed is:

1. A method for exciting chemical bonds in molecules using an electromagnetic field, comprising the steps of:
   generating a plurality of electromagnetic oscillation modes using a single energy source which belongs to a common electrical circuit, said common electric circuit also including sources of said oscillation modes, wherein time and spatial synchronism is established for said oscillation modes, said oscillation modes redistributing respective mode energies between themselves, and
   transferring energy derived from said redistribution of mode energies to at least one pair of electrons comprising a chemical bond.

2. The method of claim 1, wherein said oscillation modes interact to form a resulting electromagnetic field, said resulting electromagnetic field characterized by a vector potential which oscillates in time, does not have spatial oscillations, and has an amplitude which decreases with distance.

3. The method of claim 1, wherein said transferring step induces a magnetic moment on said pair of electrons.

4. The method of claim 1, further comprising the step of providing a self-sustained oscillation system with distributed parameters for said generating step.

5. The method of claim 4, wherein said self-sustained oscillation system comprises a generator of SHF radiation loaded on a reflecting cavity resonator.

6. The method of claim 4, wherein said self-sustained oscillation system comprises a generator of SHF radiation loaded on a reentrant cavity resonator.

7. The method of claim 4, said self-sustained oscillation system comprises a generator of SHF radiation loaded on an open (optical) resonator.

8. A method of synthesizing compounds, comprising the steps of:
   generating a plurality of electromagnetic oscillation modes, using a single energy source which belongs to a common electrical circuit, said common electric circuit also including sources of said oscillation modes, wherein time and spatial synchronism is established for said oscillation modes, said oscillation modes redistributing respective mode energies between themselves; and
   applying at least a portion of said redistributed mode energy to at least one reagent, wherein said redistributed mode energy increases the rate of formation of at least one chemical bond involving said first reagent compared to said rate in the absence of said redistributed mode energy.

9. The method of claim 8, wherein said at least one reagent comprises at least a first and second reagent.

10. The method of claim 8, further comprising the step of providing a self-sustained oscillation system with distributed parameters for said generating step.

11. The method of claim 10, wherein said self-sustained oscillation system comprises a generator of SHF radiation loaded on a reflecting cavity resonator.

12. The method of claim 10, wherein said self-sustained oscillation system comprises a generator of SHF radiation loaded on a reentrant cavity resonator.

13. The method of claim 10, wherein said self-sustained oscillation system comprises a generator of SHF radiation loaded on an open (optical) resonator.

14. The method of claim 10, wherein said method comprises formation of a crystalline material.

15. The method of claim, 14, further comprising the step of controlling said applying step to produce selected magnetic or dielectric properties of said crystalline material, said properties different from inherent ones of said properties of said material.

16. The method of claim 14, wherein said crystalline material is a single crystal.

17. A method for electromagnetically pumping chemical bonds, comprising the steps of:
   generating a plurality of electromagnetic oscillation modes, using a single energy source which belongs to a common electrical circuit, said common electric circuit also including sources of said oscillation modes, wherein time and spatial synchronism is established for said oscillation modes, said oscillation modes redistributing respective mode energies between themselves;
   applying at least a portion of said redistributed mode energy to at least one object having at least one naturally occurring anisotropic structural, mechanical or electromagnetic parameter, and
   modifying at least one of said anisotropic parameters upon transfer of at least a portion of said redistributed mode energy to said object.

18. The method of claim 17, wherein said modifying comprises changing the equilibrium energy level distribution of electrons involved in formation of chemical bonds in said object.

19. The method of claim 18, wherein said changing of the equilibrium energy level distribution of electrons comprises population inversion.

20. The method of claim 19, further comprising the step of stimulating electromagnetic emission from said object.

21. The method of claim 17, wherein said anisotropic electromagnetic parameters are (at least one) selected from the group consisting of dielectric constant, electrical conductivity, thermo-EMF.

22. The method of claim 17, further comprising providing a self-sustained oscillation system with distributed parameters for said generating step.

23. The method of claim 22, wherein said self-sustained oscillation system comprises a generator of SHF radiation loaded on a reflecting cavity resonator.

24. The method of claim 22, wherein said self-sustained oscillation system comprises a generator of SHF radiation loaded on a reentrant cavity resonator.

25. The method of claim 22, said self-sustained oscillation system comprises a generator of SHF radiation loaded on an open (optical) resonator.

26. A method for characterization of materials, comprising the steps of: generating a plurality of electromagnetic oscillation modes, using a single energy source which belongs to a common electrical circuit, said common electric circuit also including sources of said oscillation modes, wherein time and spatial synchronism is established for said oscillation modes, said oscillation modes redistributing respective mode energies between themselves;

transferring energy derived from said oscillation modes to impart energy to at least one pair of electrons comprising a chemical bond of a material;

applying a stimulating probing signal to said material, and obtaining a spectrum from said material responsive to said probing signal.

27. The method of claim 26, wherein electrons of said material are all paired.

28. The method of claim 26, wherein said material is in-vivo.

29. The method of claim 28, wherein said in-vivo material is a bacteria.

30. An apparatus for exciting chemical bonds in molecules using an electromagnetic field, comprising:

structure for generating a plurality of electromagnetic oscillation modes, and a single energy source which belongs to a common electrical circuit, said common electric circuit also including said structure for generating oscillation modes, wherein time and spatial synchronism is established for said oscillation modes, said oscillation modes redistributing respective mode energies between themselves, wherein energy derived from said redistributed mode energy is transferred to at least one pair of electrons comprising a chemical bond.

31. The apparatus of claim 30, wherein said modes interact to form a resulting electromagnetic field, said resulting electromagnetic field characterized by a vector potential which oscillates in time, does not have spatial oscillations, and has an amplitude which decreases with distance.

32. The apparatus of claim 30, further comprising a self-sustained oscillation system with distributed parameters.

33. The apparatus of claim 32, wherein said self-sustained oscillation system comprises a generator of SHF radiation loaded on a reflecting cavity resonator.

34. The apparatus of claim 32, wherein said self-sustained oscillation system comprises a generator of SHIF radiation loaded on a reentrant cavity resonator.

35. The apparatus of claim 32, wherein said self-sustained oscillation system comprises a generator of SHF radiation loaded on an open (optical) resonator.

* * * * *